United States Patent [19]

Sparks et al.

[11] Patent Number: 5,726,172
[45] Date of Patent: Mar. 10, 1998

[54] TOCOLYTIC OXYTOCIN RECEPTOR ANTAGONISTS

[75] Inventors: Michelle A. Sparks, Solebury; Roger M. Freidinger, Lansdale; Debra S. Perlow, Greenville; Peter D. Williams, Harleysville, all of Pa.

[73] Assignee: Merck & Co., Inc., Rahway, N.J.

[21] Appl. No.: 779,296

[22] Filed: Jan. 6, 1997

Related U.S. Application Data

[60] Provisional application No. 60/010,034, Jan. 16, 1996.

[51] Int. Cl.$^6$ ................ C07D 265/12; A61K 31/535
[52] U.S. Cl. ................ 514/230.5; 544/73; 544/92
[58] Field of Search ................ 544/73, 92; 514/230.5

[56] References Cited

U.S. PATENT DOCUMENTS

| | | | |
|---|---|---|---|
| 4,344,945 | 8/1982 | Teranishi et al. | 424/248.52 |
| 5,225,402 | 7/1993 | Ogawa et al. | 514/23 |
| 5,356,904 | 10/1994 | Freidinger et al. | 514/312 |

FOREIGN PATENT DOCUMENTS

| | | |
|---|---|---|
| 0382185 | 8/1990 | European Pat. Off. . |
| 0470514 | 2/1992 | European Pat. Off. . |
| 94/01113 | 1/1994 | WIPO . |
| WO 95/02405 | 1/1995 | WIPO . |

OTHER PUBLICATIONS

Chemical Abstract 125:221854 for WO96/22775 (Aug. 1, 1996), Williams et al., with Registry file printout of compounds.

J. Med. Chem., "Communications to the Editor" (1995) 38, 4634–4636, Williams et al.

Am. J. Perinatol., "Treatment of Preterm Labor with the Oxytocin Antagonist Atosiban" (1996) 13, 143–146, Goodwin et al.

Am J. Obstet. Gynecol., "The effect of the oxytocin antagonist atosiban on preterm uterine activity in the human" (1994) 170, 474–478, Goodwin et al.

*Primary Examiner*—John M. Ford
*Attorney, Agent, or Firm*—Mary A. Appollina; Melvin Winokur

[57] ABSTRACT

This invention relates to certain novel benzoxazinone compounds and derivatives thereof, their synthesis, and their use as oxytocin receptor antagonists. One application of these compounds is in the treatment of preterm labor. The ability of the compounds to relax uterine contractions in mammals also makes them useful for treating dysmenorrhea and stopping labor prior to cesarean delivery. A typical compound is as follows:

13 Claims, No Drawings

TOCOLYTIC OXYTOCIN RECEPTOR ANTAGONISTS

CROSS REFERENCE TO RELATED APPLICATIONS

This is a non-provisional application based provisional application Ser. No. 60/010,034, filed Jan. 16, 1996 (now abandoned).

FIELD OF THE INVENTION

The present invention provides novel compounds, novel compositions, methods of their use and methods of their manufacture; such compounds are generally pharmacologically useful as agents in obstetric and gynecologic therapy in mammals. More specifically, the compounds of the present invention can be used in the treatment of preterm labor, dysmenorrhea and for stopping labor preparatory to Cesarean delivery.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention are also useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist is more efficacious for treating dysmenorrhea than current regimens. An additional use for the present invention is for the stoppage of labor preparatory to Cesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating the oxytocin-related disorders of preterm labor and dysmenorrhea by antagonizing the binding of oxytocin to its receptor.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. The compounds of the present invention are therefore useful in the treatment and prevention of oxytocin-related disorders of animals, preferably mammals and especially humans. These disorders are primarily preterm labor and dysmenorrhea. The compounds are also useful for stoppage of labor preparatory to Cesarean delivery.

SUMMARY OF THE INVENTION

The compounds and their pharmaceutically acceptable salts of the present invention are of the general formula (I)

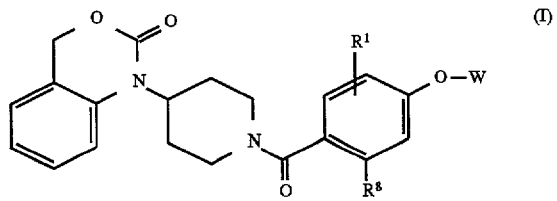

wherein $R^1$ is selected from hydrogen or halogen;

W is selected from

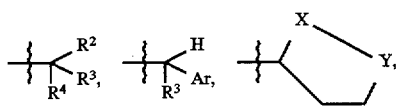

-continued

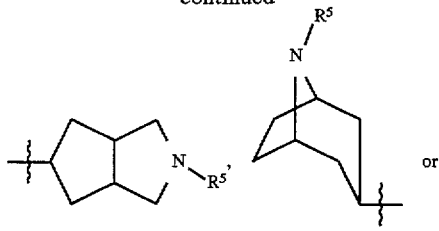

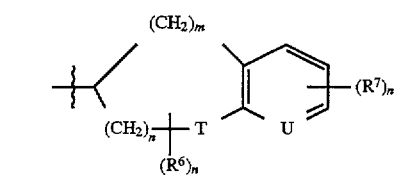

$R^2$ is selected from hydrogen, halogen or $C_{1-5}$ alkyl;
$R^3$ is selected from hydrogen, halogen, $C_{1-5}$ alkyl or Ar;
$R^4$ is selected from mono-, di- or tri-halogenated $C_{1-5}$ alkyl, $CONH_2$, $CO_2R^7$, CN, $CH_2OR^7$, $CH(CH_3)OH$, $CH_2N(R^7)_2$,

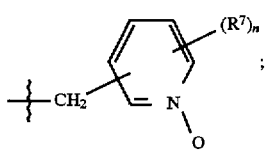

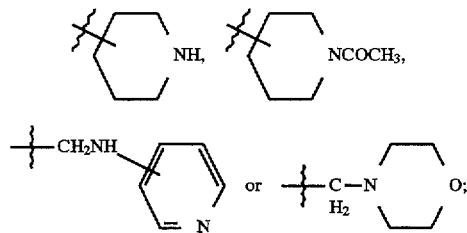

$R^5$ is selected from hydrogen, $COCH_3$, $CO_2C(CH_3)_3$ or

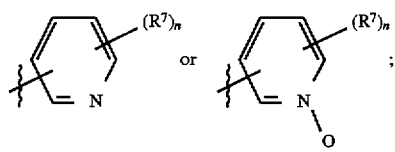

$R^6$ and $R^7$ are each independently selected from hydrogen or $C_{1-5}$ alkyl;
$R^8$ is selected from hydrogen or $C_{1-5}$ alkoxy;
T is selected from O, $CH_2$ or $SO_2$;
U is selected from CH or N;
X is selected from $(CH_2)_n$ or $CH(Ph)CH_2$;
Y is selected from O, NH, $CH_2$, $CHNH_2$, $SO_2$, $CHNHCOCH_3$, $NCOCH_3$ or CO;
Ar is selected from phenyl, trifluoromethylphenyl, naphthyl, tetrazolyl, thiazolyl, imidazolyl, pyrazinyl, pyrimidinyl,

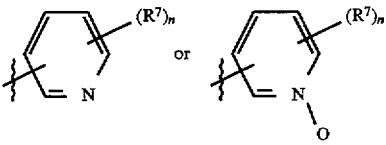

m is an integer from zero to one;
n is an integer from zero to three;
provided that when $R^1$ is hydrogen and $R^8$ is $C_{1-5}$ alkoxy and W is

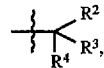

and X is $(CH_2)_n$, then Y is selected from O, $CH_2$, $CHNH_2$, $SO_2$, $CHNHCOCH_3$ or CO;
provided further that when $R^1$ is hydrogen and W is

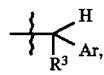

and $R^2$ and $R^3$ are both hydrogen, then $R^4$ is selected from mono-, di- or tri-halogenated $C_{1-5}$ alkyl, $CONH_2$, $CO_2R^7$, CN, $CH_2OR^7$, $CH(CH_3)OH$, $CH_2N(R^7)_2$,

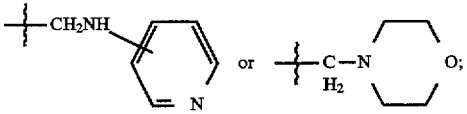

provided further that when $R^1$ is hydrogen and $R^8$ is $C_{1-5}$ alkoxy and W is

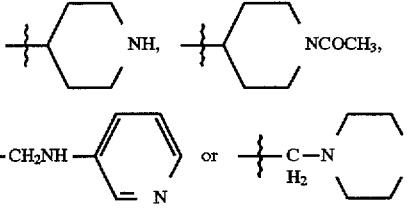

and $R^3$ is hydrogen, then Ar is selected from trifluoromethylphenyl, naphthyl, tetrazolyl, thiopyrazolyl, imidazolyl, pyrazinyl, pyrimidinyl, and the pharmaceutically acceptable salts thereof.
In one embodiment of the present invention is the compound wherein
$R^1$ is selected from hydrogen or fluorine;
$R^2$ is selected from hydrogen or fluorine;
$R^3$ is selected from hydrogen, fluorine, methyl or phenyl;
$R^4$ is selected from $(CH_2)_nF$, $(CH_2)_mCHF_2$, $(CH_2)_mCF_3$, $CONH_2$, $CO_2H$, $CO_2CH_3$, CN, $CH_2OH$, $CH_2OCH_3$, $CH(CH_3)OH$, $CH_2N(Et)_2$, $R^6$ is selected from hydrogen or methyl;
$R^7$ is selected from hydrogen, methyl, ethyl or isopropyl;
$R^8$ is methoxy;
and all other variables are as defined above;

provided that when $R^1$ is hydrogen and W is

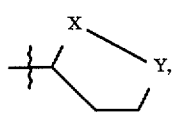

and X is $(CH_2)_n$, then Y is selected from O, $CH_2$, $CHNH_2$, $SO_2$, $CHNHCOCH_3$ or CO;

provided further that when $R^1$ is hydrogen and W is

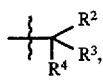

and $R^2$ and $R^3$ are both hydrogen, then $R^4$ is selected from $(CH_2)_nF$, $(CH_2)_mCF_2$, $(CH_2)_mCF_3$, $CONH_2$, $CO_2H$, $CO_2CH_3$, CN, $CH_2OH$, $CH_2OCH_3$, $CH(CH_3)OH$, $CH_2N(Et)_2$,

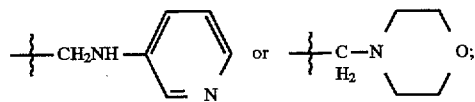

provided further that when $R^1$ is hydrogen and W is

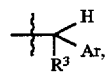

and $R^3$ is hydrogen, then Ar is selected from trifluoromethylphenyl, naphthyl, tetrazolyl, thiopyrazolyl, imidazolyl, pyrazinyl, pyrimidinyl,

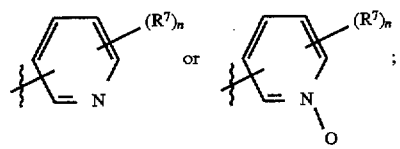

and the pharmaceutically acceptable salts thereof.

In a class of the invention is the compound of the formula

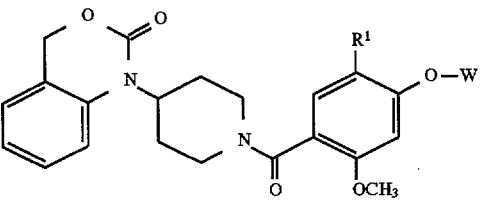

where all variables are as defined above;
and the pharmaceutically acceptable salts thereof.

In a subclass of the invention is the compound of the formula

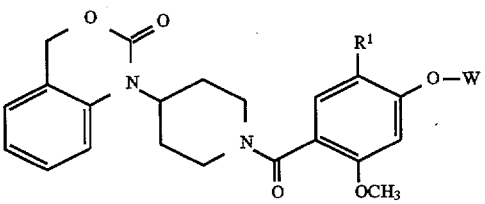

wherein W is selected from

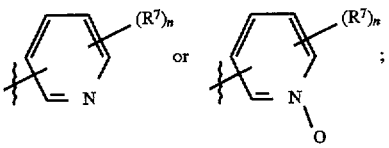

and where all other variables are as defined above;
and the pharmaceutically acceptable salts thereof.

Illustrative of the invention is the compound wherein
$R^2$ is hydrogen;
$R^3$ is selected from hydrogen or methyl;
$R^4$ is selected from $(CH_2)_nF$, $(CH_2)_mCHF_2$ or $(CH_2)_mCF_3$;
Ar is selected from X is $(CH_2)_n$;
Y is O;
and where all other variables am as defined above;
and the pharmaceutically acceptable salts thereof.

Exemplifying the invention is the compound selected from

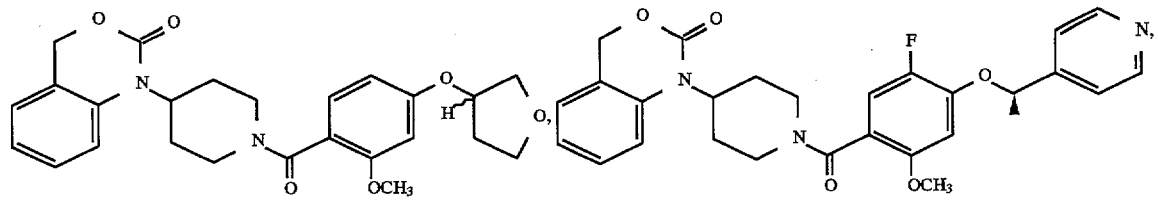

-continued

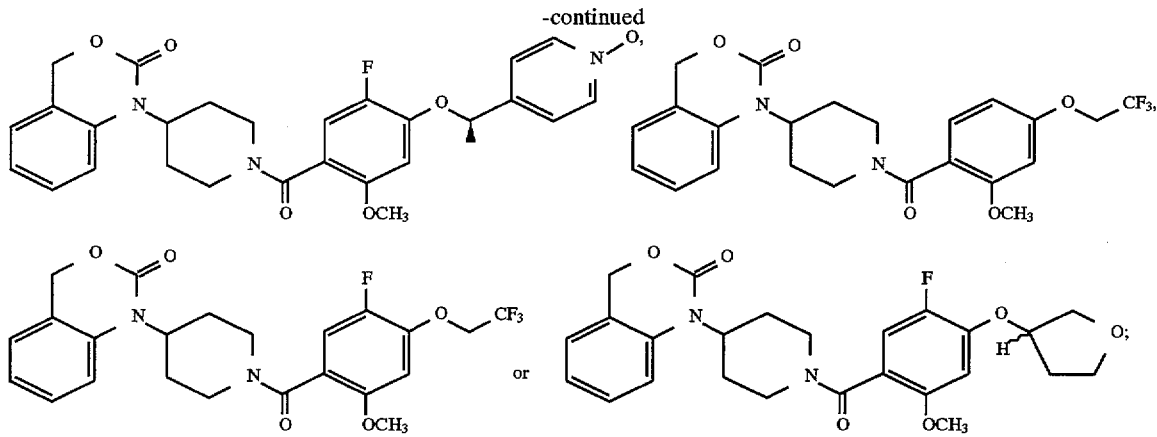

and the pharmaceutically acceptable salts thereof.

An illustration of the invention is a pharmaceutical composition comprising a pharmaceutically acceptable carrier and a therapeutically effective amount of any of the compounds described above.

Further illustrating the invention is a method of eliciting an oxytocin antagonizing effect in a mammal in need thereof, comprising administering to the mammal a therapeutically effective amount of any of the compounds described above to elicit an oxytocin antagonizing effect.

An example of the invention are methods of treating preterm labor, stopping labor preparatory to cesarean delivery, and treating dysmenorrhea in a mammal in need thereof, comprising administering to the mammal a therapeutically effective amount of any of the compounds described above.

Further exemplifying the invention is the use of any of the compounds described above in the preparation of a medicament for the treatment of preterm labor, dysmenorrhea or stoppage of labor prior to cesarean delivery in a mammal in need thereof.

More particularly illustrating the invention is a drag which is useful for treating preterm labor, dysmenorrhea or stopping labor prior to cesarean delivery in a mammal in need thereof, the effective ingredient of the said drug being any of the compounds described above.

More specifically exemplifying the invention are methods of increasing fertility and embryonic survival in a farm animal in need thereof, and controlling the timing of estrus in a farm animal in need thereof, comprising administering to the farm animal a therapeutically effective amount of any of the compounds described above.

Another example of the invention is a method for improving survival of a farm animal neonate comprising controlling timing of parturition to effect delivery of the neonate during daylight hours by administering to a farm animal which is expected to deliver the neonate within 24 hours a therapeutically effective amount of any of the compounds described above.

Additional illustrations of the instant invention are methods of antagonizing vasopressin from binding to its receptor site, inducing vasodilation, treating hypertension, inducing diuresis and inhibiting platelet agglutination in a mammal in need thereof comprising the step of administering to the mammal a therapeutically effective amount of any of the compounds described above.

DETAILED DESCRIPTION OF THE INVENTION

Representative compounds of the present invention are selective oxytocin antagonists which display submicromolar affinity for the human oxytocin receptor. Preferred compounds of this invention were found to have $IC_{50}$ values for the human oxytocin receptor in the range of 5–500 nM.

The compounds of the present invention are administered in dosages effective to antagonize the oxytocin receptor where such treatment is needed, as in the treatment of preterm labor. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range (i.e., methyl, ethyl, 1-propyl, 2-propyl, n-butyl, t-butyl, etc.).

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent.

Where multiple substituent moieties are disclosed or claimed, the substituted compound can be independently substituted by one or more of the disclosed or claimed substituent moieties, singly or plurally.

The variable "n", which was previously defined as "an integer from 0 to 3" also includes within its scope any subset within this range, e.g., 1 to 3, 1 to 2, 2 to 3, 0 to 2.

The term "preterm labor" shall mean expulsion from the uterus of a viable infant before the normal end of gestation, or more particularly, onset of labor with effacement and dilation of the cervix before the 371th week of gestation. It may or may not be associated with vaginal bleeding or rupture of the membranes.

The term "dysmenorrhea" shall mean painful menstruation.

The term "Cesarean delivery" shall mean incision through the abdominal and uterine walls for delivery of a fetus.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and dysmenorrhea. These compounds may also find usefulness for stoppage of labor preparatory to Cesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

The present invention is also directed to combinations of the compounds of formula I with one or more agents useful in the treatment of oxytocin related disorders such as preterm labor, dysmenorrhea and stopping labor prior to cesarean delivery. For example, the compounds of the instant invention may be effectively administered in combination with effective amounts of other agents used in the treatment of preterm labor, such as antenatal steroids (e.g., dexamethasone). Preferred combinations are simultaneous or alternating treatments of an oxytocin receptor antagonist of the present invention and an antenatal steroid. These combinations have beneficial effects on the neonate by both decreasing uterine activity to prolong gestation and increasing fetal maturation. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating oxytocin related conditions includes in principle any combination with any pharmaceutical composition useful for treating preterm labor, dysmenorrhea or stopping labor prior to cesarean delivery.

The oxytocin antagonist compounds of the present invention are also useful for improving reproductive efficiency in farm animals. In certain farm animals (e.g., sheep, cattle, swine, horses and goats), the beginning of the estrous cycle is typically marked by behavioral estrus when the female animal accepts the male for mating. Ovulation of the ovarian follicle occurs shortly after onset of estrus and cells in the follicle give rise to the corpus luteum. The cells that form the corpus luteum produce progesterone and they also produce oxytocin. The secretion of oxytocin from the corpus luteum and/or pituitary acts on the uterine endometrium to stimulate the secretion of prostaglandins (in particular PGF) which, in turn, causes the regression of the corpus luteum of the ovary. PGF is, therefore, the luteolytic hormone. In the cycling animal (i.e., where mating and fertilization have not occurred), destruction of the corpus luteum removes the source of progesterone which is key to the preparation of the uterus for pregnancy. The presence of a viable conceptus (i.e., the embryo and its associated membranes) is necessary to prevent the luteolytic process. In fact, the first key signal that the conceptus must produce is the one to prevent regression of the corpus luteum (i.e., the maternal recognition of pregnancy signal). Thus, in the animal where mating and fertilization have occurred, the conceptus secretes a factor that antagonizes the action of oxytocin to induce luteolysis. This results in maintenance of a functioning corpus luteum and the continued secretion of progesterone which is obligatory to the initiation of pregnancy.

Administration of an oxytocin antagonist of the present invention at this critical period after fertilization (i.e., just prior to or during the period of maternal recognition of pregnancy) supplements the natural signal from the conceptus (i.e., maternal recognition of pregnancy) to prolong corpus luteal function. The result is to increase pregnancy rates by enhancing the chances of impregnation through a reduction in embryonic loss. Thus, to improve fertility and embryonic survival in a farm animal, a mated animal, for example, a mated ewe, is treated with an oxytocin antagonist compound beginning on between day 10 to day 15 after onset of estrus. The oxytocin antagonist compound is administered to the mated animal for a period of one day to three weeks, preferably one week to three weeks, most preferably one week to two weeks.

The compounds of the present invention are also useful for controlling the timing of parturition in farm animals so that delivery of the neonates occurs during the daytime. Approximately 80% of livestock are delivered at night and up to 5 to 10% of newborns die because the deliveries are not monitored properly. An oxytocin antagonist compound of the present invention administered to the mother on the evening before expected delivery delays parturition so that the delivery occurs during the daylight hours. By delaying the timing of parturition, proper monitoring of the delivery and the neonates is ensured, resulting in increased survival rates of the newborns.

In addition, the oxytocin antagonists of the instant invention can also be used to control the timing of estrus in a cycling farm animal by preventing luteal regression. An oxytocin antagonist compound of the instant invention is administered to a cycling farm animal prior to expected estrus to prevent regression of the corpus luteum. Daily administration of the compound retards estrus until administration of the compound ceases. Preferably, the oxytocin antagonist compound is administered at least 1 day prior to expected estrus. By delaying estrus in a group of farm animals, a farmer can synchronize estrus among the group to provide time and cost savings in farm management.

The compounds of the present invention also bind to the vasopressin receptor and are therefore useful as vasopressin antagonists. Vasopressin antagonists are useful in the treatment or prevention of disease states involving vasopressin disorders; thus, the compounds are useful for inducing vasodilation, treating hypertension, inducing diuresis, inhibiting platelet agglutination and treating congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.0025 to 5.0 gm/day orally. More particularly, when administered orally for the treatment of preterm labor, an effective daily dose will be in the range of 0.05 mg/kg to about 100 mg/kg of body weight, preferably, from 0.1 mg/kg to 50 mg/kg, administered in single or divided dose. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethyl-aspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Abbreviations used in the instant specification, particularly the Schemes and Examples, are as follows:

Bn=benzyl
Boc=t-butyloxycarbonyl
BOP=benzotriazol-1-yloxytris(dimethylamino) phosphonium hexafluorophosphate DCC=1,3-dicyclohexylcarbodiimide
DCM=dichloromethane
DEAD=diethyl azodicarboxylate
DIEA=diisopropylethylamine
DMAP=4-dimethylaminopyridine
DMF=dimethylformamide
DMSO=dimethyl sulfoxide
Et=ethyl
EtOAc=ethyl acetate
EtOH=ethanol
EDC=1-ethyl-3-(3-dimethylaminopropyl)carbodiimide
FAB MS=fast atom bombardment mass spectroscopy
HOAc=acetic acid
HOBT or HBT=1-hydroxybenzotriazole
HPLC=high performance liquid chromatography
IPA=isopropyl acetate
LDA=lithium diisopropylamide
m-CPBA or MCPBA=meta-chloroperoxybenzoic acid
Me=methyl
MeOH=methanol
MOM=methoxymethyl
NCS=N-chlorosuccinimide
NMR=nuclear magnetic resonance
Ph=phenyl
PPTS=pyridinium p-toluenesulfonate
TFA=trifluoroacetic acid
THF=tetrahydrofuran
TLC=thin layer chromatography
TMEDA=N, N, N', N'-tetramethylethylenediamine
TMS=trimethylsilyl
TMS-allyl=allyltrimethylsilane The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail.

Scheme I

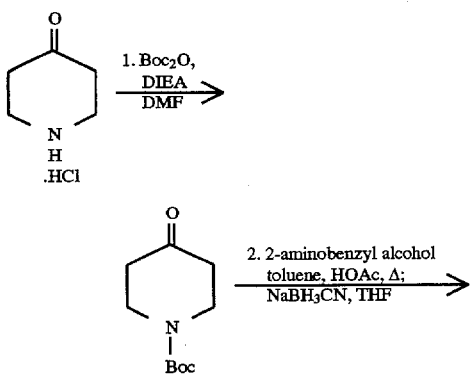

-continued
Scheme I

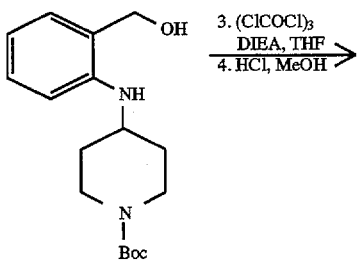

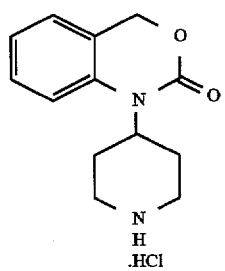

Step 1. To a stirred, 0° C. solution of 4-piperidinone hydrochloride hydrate (50 g, 330 mmol) in DMF (500 mL) was added di-t-butyldicarbonate (64 g, 290 mmol) followed by a dropwise addition of DIEA (63 mL, 360 mmol). After the addition of DIEA was complete, the reaction was allowed to gradually warm to ambient temperature over 4 h and stirring was continued for 20 h. The DMF was removed under reduced pressure and the residue was dissolved in EtOAc (1000 mL) and washed with 5% aqueous citric acid (2×500 mL), water (250 mL), and saturated aqueous $NaHCO_3$ (500 mL). The EtOAc layer was dried ($Na_2SO_4$), filtered, and the EtOAc was removed under reduced pressure. The residue was boiled in ether (ca. 250 mL) until the solid had dissolved. Cooling gave N-t-butyloxycarbonyl-4-piperidinone as white crystals.

Step 2. N-t-butyloxycarbonyl-4-piperidinone (20 g, 100 mmol) from Step 1, 2-aminobenzyl alcohol (13 g, 110 mmol), and acetic acid (14 mL, 220 mmol) were dissolved in dry toluene (500 mL). The solution was refluxed under inert atmosphere with azeotropic removal of water for 16 h. The solution was cooled to ambient temperature and to it was added $NaBH_3CN$ (14 g, 220 mmol) and dry THF (200 mL). The reaction was stirred at ambient temperature for 24 h. The reaction was concentrated under reduced pressure and the residue was dissolved in EtOAc (750 mL). The EtOAc layer was washed with saturated aqueous $NaHCO_3$ (4×500 mL) and brine (250 mL). The EtOAc layer was dried ($MgSO_4$), filtered, and the solvent was removed under reduced pressure. The residue was purified by pressurized silica gel column chromatography, using a gradient elution of 15–30% EtOAc-hexanes. 1-t-Butyloxycarbonyl-4-((2-hydroxymethyl)phenylamino)piperdine was obtained as a gum.

Step 3. 1-t-Butyloxycarbonyl-4-((2-hydroxymethyl)phenylamino)-piperdine (24 g, 78 mmol) from Step 2 was dissolved in dry THF (250 mL) and cooled to 0° C. To the solution was added DIEA (41 mL, 240 retool) and triphosgene (8.54 g, 28.8 mmol). The reaction was stirred at 0° C. for 1 h, and then at ambient temperature for 72 h. Ether (250 mL) was added, the mixture was cooled to 0° C. for 3 h and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous NaHCO₃ (2×500 mL). The EtOAc layer was dried (MgSO₄), filtered, and the solvent was removed under reduced pressure. The residue was boiled in ether (ca. 200 mL) until the solid had dissolved. Cooling overnight gave 1-((1-t-butyloxycarbonyl)piperidin-4-yl)-1,2-dihydro-4(H)-3,1-benzoxazin-2-one as off-white crystals.

Step 4. A stirred solution of 1-((1-t-Butyloxycarbonyl) piperidin-4-yl)-1,2-dihydro-4(H)-3,1-benzoxazin-2-one (19 g, 57 mmol) from Step 3 in EtOAc (500 mL) was cooled to 0° C. HCl gas was bubbled through the solution for 30 min. Stirring was continued at 0° C. for 1 h, during which time a precipitate had formed, and then at ambient temperature for 1 h. The stirred suspension was cooled to 0° C. and cold ether (250 mL) was added. After 1 h at 0° C., the solid was collected by filtration. The solid was dried under reduced pressure for 18 h, giving the hydrochloride salt of 1-(4-piperidinyl)-1,2-dihydro-4(H)-3,1-benzoxazin-2-one as an off-white solid.

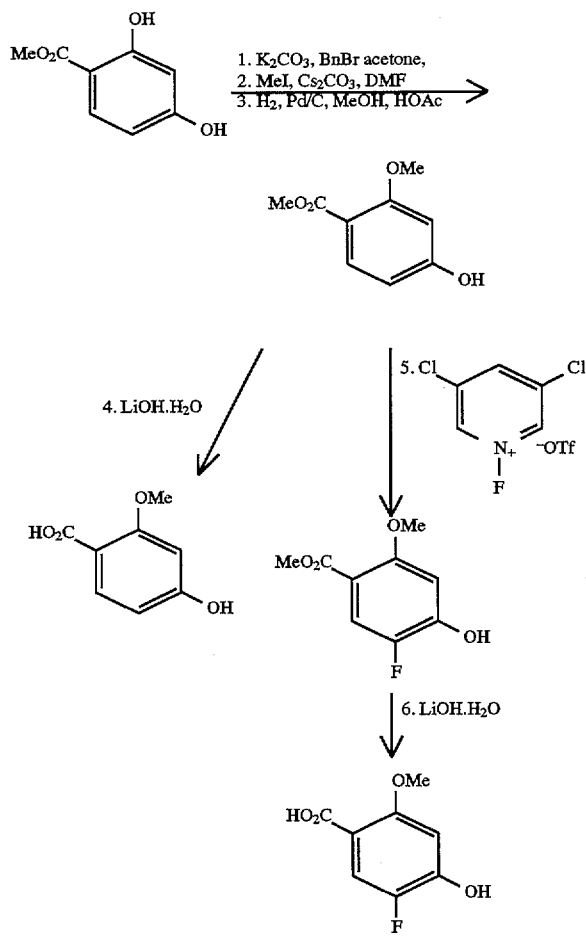

Scheme II

Step 1. To a stirred, 0° C. solution of methyl 2,4-dihydroxybenzoate (50 g, 300 mmol) in acetone (1000 mL) was added K₂CO₃ (150 g, 1000 mmol) and benzyl bromide (330 mmol, 39 mL). The solution was allowed to warm to ambient temperature over 48 h. The reaction solution was filtered through celite and the acetone solution stripped down under reduced pressure. The crude oil was dissolved in EtOAc (1000 mL) and washed with water (250 mL), and saturated aqueous NaHCO₃ (500 mL). The EtOAc layer was dried (MgSO₄), filtered, and the EtOAc was removed under reduced pressure. The crude product was purified by pressurized silica gel column chromatography using 5:1 hexanes:EtOAc. Evaporation of the hexanes:EtOAc mixture gave the desired methyl 4-benzyloxy-2-hydroxybenzoate as a white powder.

Step 2. To a stirred, 0° C. solution of methyl 4-benzyloxy-2-hydroxybenzoate (12 g, 46 mmol) in DMF (150 mL) was added NaH (2.76 g, 69 mmol) and methyl iodide (7.2 mL, 116 mmol). The solution was allowed to warm to ambient temperature overnight with stirring. The reaction mixture was poured onto ice and the resulting aqueous solution extracted with Et₂O (3×200 mL). The organic phase was dried (MgSO₄), filtered and the Et₂O removed under reduced pressure. The crude white solid was purified by pressurized silica gel column chromatography using 4:1 hexanes:EtOAc. Evaporation of the hexanes:EtOAc mixture gave the desired methyl 4-benzyloxy-2-methoxybenzoate as a white powder.

Step 3. To a clean, dry 500 mL round bottom flask was added the methyl 4-benzyloxy-2-methoxybenzoate (16.48 g, 60 mmol). The flask was pumped and purged with Argon 4 times and the palladium catalyst was added (10% Pd/C, 2 g). Methanol (200 mL) was slowly added and then HOAc (2 mL). The solution was placed under 1 atm of H₂ (balloon) and stirred overnight. The methanol solution was filtered through celite and the crude reaction solution stripped down to afford an oil. The product was purified by pressurized silica gel column chromatography using 1:1 hexanes:EtOAc. Evaporation of the hexanes:EtOAc mixture gave the desired methyl 4-hydroxy-2-methoxybenzoate as a white powder.

Step 4. To a stirred solution of methyl 4-hydroxy-2-methoxybenzoate (11 g, 60 mmol) in THF:H₂O (100 mL:10 mL) was added LiOH.H₂O (3 g, 71 mmol). The solution was stirred over 24 h and then made slightly acidic (pH 5) with 10% HCl (approx 15 mL). The reaction solution was extracted with CH₂Cl₂ (3×50 mL). The organic phase was dried (MgSO₄) and filtered. The solvent was evaporated under reduced pressure to afford the 4-hydroxy-2-methoxybenzoic acid as a clean white foam.

In the cases where the 5-fluoro-2-methoxy-4-hydroxy benzoic acid was the desired intermediate, the following procedures were followed:

Step 5: To a stirred solution of the methyl 4-hydroxy-2-methoxybenzoate (1 g, 5 mmol, from Step 3) in CH₂Cl₂ (20 mL) was added 3,5-dichloro-1-fluoropyridinium triflate (2.25 g, 6 mmol). The solution was refluxed for 48 h and then cooled to ambient temperature and stripped down under reduced pressure. The crude oil was purified by pressurized silica gel column chromatography using 99:1 CH₂Cl₂:MeOH. Evaporation of the CH₂Cl₂:MeOH mixture gave the desired methyl 5-fluoro-4-hydroxy-2-methoxybenzoate as a white powder.

Step 6. This reaction is similar to the reaction conditions outlined in step 4. The methyl 5-fluoro-4-hydroxy-2-methoxybenzoate (0.5 g, 3 mmol) was saponified to the 5-fluoro-4-hydroxy-2-methoxybenzoic acid.

Scheme III

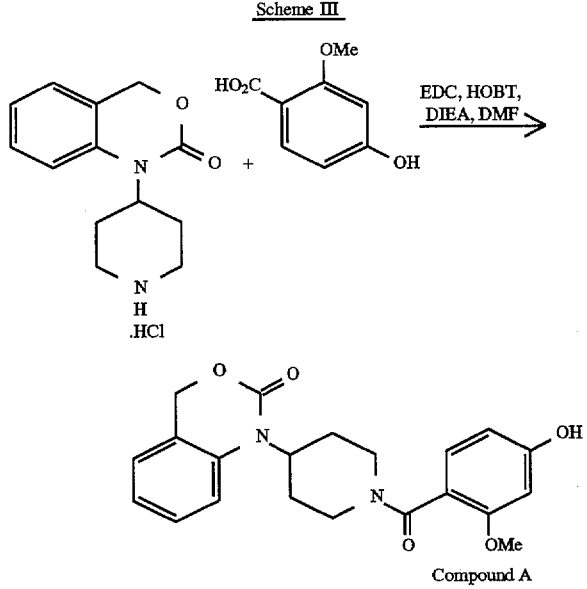

Compound A

To a solution of benzoic acid (1.0 g, 6 mmol) in DMF (20 mL) was added EDC (1.5 g, 8 mmol), HOBT (1.2 g, 8 mmol) and DIEA (titrated to pH 8, approx 1.0 mL). This solution was stirred for 1 h and then the 1-(4-piperidinyl)-1,2-dihydro-4(H)-3,1-benzoxazin-2-one (1.4 g, 6 mmol) was added. The resulting mixture was stirred overnight and then the DMF was removed under reduced pressure. The crude mixture was dissolved in $CH_2Cl_2$ (30 mL) and washed with saturated citric acid (2×20 mL), $H_2O$ (2×20 mL) and brine (2×20 mL). The organic phase was dried ($MgSO_4$) and filtered. The solvent was evaporated under reduced pressure to afford a yellow foam. The crude solid was purified by pressurized silica gel column chromatography using 98:2 $CH_2Cl_2$:MeOH($NH_3$). Evaporation of the $CH_2Cl_2$:MeOH ($NH_3$) mixture gave 1-{1-[4-hydroxy-2-methoxybenzoyl]-piperdin-4-yl}-4H-3,1-benzoxazin-2(1H)-one, referred to hereinafter as Compound A, as a white powder.

The most preferred compounds of the invention are any or all of those specifically set forth in the following Examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

All solvents were reagent grade and stored over 4 Å molecular sieves. THF was distilled from calcium hydride under inert atmosphere. Dioxane was dried and freed of peroxides by passage through a column of activity I neutral alumina. MeOH($NH_3$) refers to a methanol solution saturated with $NH_3$ gas at 0° C.

Determination of reaction pH was estimated by spotting an aliquot from the reaction mixture on wetted E. Merck pH sticks. $^1H$ NMR spectra were measured at 300 MHz on a Varian XL-300, at 400 MHz on a Varian XL-400, and at 360 MHz on a Nicolet NT-360 using $(CH_3)_4Si$ as an internal standard NMRs for all of the compounds in the Examples which follow were consistent with structures. Fast atom bombardment mass spectra (FAB MS) were obtained on a VG-ZAB-HF spectrometer.

Analytical HPLC were run on a Spectra Physics SP4270/8800 instrument using the following conditions:

| Column: Vydac $C_{18}$, 0.21 × 15 cm |  |
|---|---|
| UV detection at 214 nm | |
| Mobile Phases | A = 0.1% by volume TFA in $H_2O$; B = MeOH; C = 0.1% by volume TFA in acetonitrile |
| Method A: | |
| Gradient | T = 0 min, 95% A, 5% C |
|  | T = 15 min, 5% A, 95% C |
| Flow = 2.0 mL/min | |

Pressurized silica gel column chromatography using 230–400 mesh silica gel was performed according to the method of Still, Kahn, and Mitra (*J. Org. Chem.* (1978) vol. 43, p.2923). Silica coated TLC plates were used to monitor all reactions (E. Merck, 5×10 cm Silica Gel 60 $F_{254}$).

EXAMPLE 1

1-{1-[4-(tetrahydro-4H-pyran-4-oxy)-2-methoxybenzoyl]-piperidin-4-yl}-4H-3,1-benzoxazin-2(1H)-one

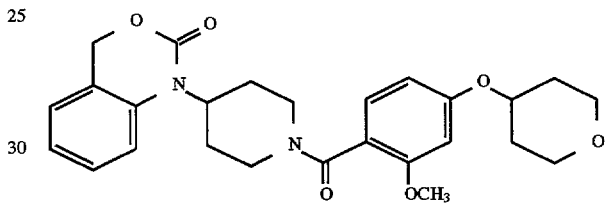

Step 1. To a stirred solution of methyl 4-hydroxy-2-methoxybenzoate (713 mg, 3.92 mmol) in dry THF (7.5 mL) was added triphenylphosphine (1.42 g, 5.4 mmol) and the solution was cooled to 0° C. A 2.5 mL volume of tetrahydro-4H-pyran-4-ol (466 mL, 4.90 mmol) and diethyl azodicarboxylate (850 μL, 5.4 mmol) in THF was added dropwise via addition funnel over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-(4-tetrahydropyranoyloxy)-2-methoxy-benzoate.

Step 2. To a stirred solution of methyl 4-(4-tetrahydropyranoyloxy)-2-methoxy-benzoate (369 mg, 1.38 mmol) in THF:$H_2O$ (2.5 mL: 0.5 mL) was added LiOH.$H_2O$ (116.4 mg, 2.77 mmol). The reaction was heated to 45° C. over 12 h and then cooled to ambient temperature. The solvent was removed under reduced pressure. The crude solid was passed through a small plug of silca gel packed in 80:20 hexanes:EtOAc and eluted with 50:50 hexanes:EtOAc. The solvent was removed under reduced pressure to afford 4-(4-tetrahydropyranoyloxy)-2-methoxy-benzoic acid as a foam.

Step 3. To a stirred solution of 4-(4-tetrahydropyranoyloxy)-2-methoxy-benzoic acid (280 mg, 1.11 mmol) in DMF (7.0 mL) was added EDC (250 mg, 1.3 mmol), HOBT (199 mg, 1.3 mmol) and then 1-(4-piperidinyl)-1,2-dihydro-4(H)-3,1-benzoxazin-2-one (309 mg, 1.3 mmol). The pH of the solution was adjusted to 8.5 (wetted E. Merck pH sticks) using diisopropylethylamine. The solution was stirred for 20 hours. The solvent was removed under reduced pressure and the residue was partitioned between CH$_2$Cl$_2$ (10 mL) and 4% aqueous HCl (10 mL). The organic phase was then extracted with water (10 mL), saturated aqueous sodium bicarbonate solution, and brine. The organic phase was dried (MgSO$_4$), filtered and the solvent was removed under reduced pressure. The residue was chromatographed on a silica gel column packed in 98:2 CH$_2$Cl$_2$:MeOH and eluted with same. The appropriate fractions were combined and the solvent removed under reduced pressure to afford a white foam. The foam was dissolved in 95:5 water:acetonitrile and freeze dried giving the title compound as a lyophilized solid.

Analysis calculated for (C$_{26}$H$_{30}$N$_2$O$_6$.0.35 CH$_2$Cl$_2$.0.30 DMF) C, 63.16; H, 6.38; N, 6.22 Found C, 63.18; H, 6.23; N, 6.37

TLC: R$_f$=0.7 in [10% MeOH(NH$_3$)/90% CH$_2$Cl$_2$]

HPLC (method A): retention time 7.69 min.

FAB MS: m/z 467 (M$^+$+H)

EXAMPLE 2

1-{1-[4-(diphenylmethoxy)-2-methoxybenzoyl]-piperidin-4-yl}-4H-3,1-benzoxazin-2(1H)-one

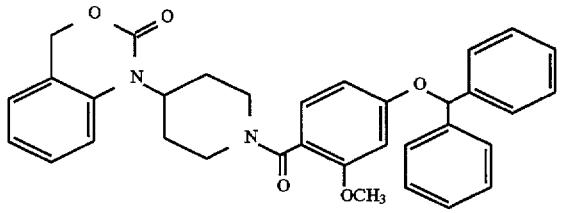

To a stirred solution of Compound A (100 mg, 0.26 mmol) in dry DMF (5 mL) was added cesium carbonate (170 mg, 0.52 mmol) followed by bromodiphenylmethane (128 mg, 0.52 mmol) and the reaction was warmed to 50° C. under argon and stirred for 18 hours. The reaction was filtered and the solvent was removed under reduced pressure. The residue was partitioned between EtOAc (100 mL) and 4% aqueous HCl (100 mL). The organic layer was washed with saturated sodium bicarbonate solution (100 mL), water, and brine and dried with MgSO$_4$ and filtered. The solvent was removed from the filtrate under reduced pressure to give a foam which was chromatographed on a silica gel column packed in 98:2 CH$_2$Cl$_2$:MeOH and eluted with the same. The appropriate fractions were combined and the solvent was removed under reduced pressure to give an oil which was dissolved in 9:1 acetonitrile: water and freeze dried giving the title compound as a lyophilized solid. Analysis calculated for (C$_{34}$H$_{32}$N$_2$O$_5$.0.7 H$_2$O) C, 72.75; H, 6.00; N, 4.99 Found C, 72.76; H, 6.01; N, 5.01

TLC: R$_f$=0.55 in 5% MeOH/95% CH$_2$Cl$_2$

HPLC (method A): retention time 11.69 min.

FAB MS: m/z 549 (M$^+$+H)

EXAMPLE 3

1-{1-[4-(N-{tert-butylcarbonyl}-3-azabicyclo-[3.3.0]-octanyl-7-oxy)-2-methoxybenzoyl]-piperidin-4-yl}-4H-3,1-benzoxazin-2(1H)-one

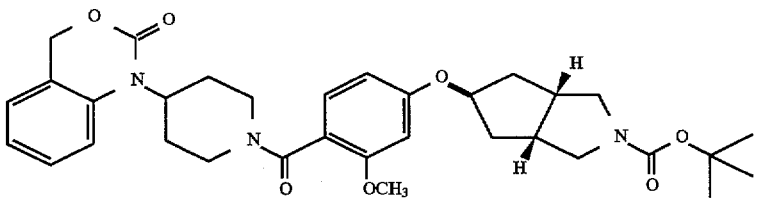

For a procedure for the preparation of N-Boc-azabicyclo-[3.3.0]-octanone see Tetrahedron Letters 1993, 34, 2087–2090.

Step 1. A stirred solution of N-Boc-azabicyclo-[3.3.0]-octanone (1.25 g, 5.6 mmol) in MeOH (20 mL) was cooled to 0° C. under Argon and treated with NaBH$_4$ (210 mg, 5.6 mmol). The reaction was stirred over 16 h and allowed to warm to ambient temperature. The solvent was removed under reduced pressure and the crude oil was chromatographed on a silica gel column packed in 95:5 EtOAc: hexanes and eluted with same. The appropriate fractions were combined and the solvent was removed under reduced pressure to give N-Boc-azabicyclo-[3.3.0]-octanol.

Step 2. To a stirred solution of methyl 4-hydroxy-2-methoxybenzoate (965 mg, 5.3 mmol) in dry THF (5 mL) was added triphenylphosphine (1.4 g, 5.3 mmol) and the solution was cooled to 0° C. A 2 mL volume of N-Boc-azabicyclo-[3.3.0]-octanol (800 mg, 3.5 mmol) and diethyl azodicarboxylate (832 μL, 5.3 mmol) in THF was added dropwise via addition funnel over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-(N-Boc-azabicyclo-[3.3.0]-octanoyloxy)-2-methoxybenzoate.

Step 3. To a stirred solution of 4-(N-Boc-azabicyclo-[3.3.0]-octanoyloxy)-2-methoxybenzoate (965 mg, 2.5 mmol) in THF:H$_2$O (5 mL: 1 mL) was added LiOH.H$_2$O (207 mg, 5 mmol). The reaction was heated to 45° C. over 12 h and then cooled to ambient temperature. The solvent was removed under reduced pressure. The crude solid was passed through a plug of silca gel packed in 80:20 hexanes:EtOAc and eluted with same. The solvent was removed under reduced pressure to afford 4-(N-Boc-azabicyclo-[3.3.0]-octanoyloxy)-2-methoxybenzoic acid as a foam.

Step 4. To a stirred solution of 4-(N-Boc-azabicyclo-[3.3.0]-octanoyloxy)-2-methoxybenzoic acid (646 mg, 1.71 mmol) in DMF (16 mL) was added EDC (383 mg, 2.05 mmol), HOBT (306 mg, 2.05 mmol) and then 1-(4-piperidinyl)-1,2-dihydro-4(H)-3,1-benzoxazin-2-one (465 mg, 2 mmol). The pH of the solution was adjusted to 8.5 (wetted E. Merck pH sticks) using diisopropylethylamine. The solution was stirred for 18 hours. The solvent was removed under reduced pressure and the residue was partitioned between CH$_2$Cl$_2$ (25 mL) and 4% aqueous HCl (20 mL). The organic phase was then extracted with water (20 mL), saturated aqueous sodium bicarbonate solution, and brine. The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent was removed under reduced pressure to give an oil which was dissolved in 9:1 acetonitrile: water and freeze dried giving the title compound as a lyophilized solid.

Analysis calculated for (C₃₃H₄₁N₃O₇.0.55 CH₂Cl₂, 0.15 MeOH) C, 62.92; H, 6.69; N, 6.53 Found C, 62.89; H, 6.64; N, 6.87

TLC: R_f=0.90 in [10% MeOH(NH₃)/90% CH₂Cl₂]

HPLC (method A): retention time 10.34 min.

FAB MS: m/z 592 (M⁺+H)

EXAMPLE 4

(±)-1-{1-[4-(1-indanyloxy)-2-methoxybenzoyl]-piperidin-4-yl}-4H-3,1-benzoxazin-2(1H)-one

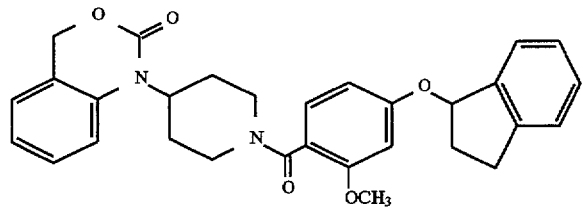

Step 1. To a stirred solution of methyl 4-hydroxy-2-methoxybenzoate (295 mg, 1.62 mmol) in dry THF (1.25 mL) was added triphenylphosphine (425 mg, 1.62 mmol) and the solution was cooled to 0° C. A 500 mL volume of 1-indanol (145 mg, 1.08 mmol) and diethyl azodicarboxylate (255 mL, 1.62 mmol) in THF was added dropwise via syringe over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-(1-indanoyloxy)-2-methoxy-benzoate.

Step 2. To a stirred solution of methyl 4-(1-indanoyloxy)-2-methoxy-benzoate (125 mg, 0.43 mmol) in THF:H₂O (1 mL: 0.2 mL) was added LiOH.H₂O (35.2 mg, 0.84 mmol). The reaction was heated to 45° C. over 12 h and then cooled to ambient temperature. The solvent was removed under reduced pressure. The crude solid was passed through a small plug of silca gel packed in 80:20 hexanes:EtOAc and eluted with 50:50 hexanes:EtOAc. The solvent was removed under reduced pressure to afford 4-(1-indanoyloxy)-2-methoxy-benzoic acid as a foam.

Step 3. To a stirred solution of 4-(1-indanoyloxy)-2-methoxy-benzoic acid (83.5 mg, 0.29 mmol) in DMF (3.5 mL) was added EDC (67 mg, 2.05 mmol), HOBT (53.5 mg, 0.35 mmol) and then 1-(4-piperidinyl)-1,2-dihydro-4(H)-3,1-benzoxazin-2-one (81 mg, 0.35 mmol). The pH of the solution was adjusted to 8.5 (wetted E. Merck pH sticks) using diisopropylethylamine. The solution was stirred for 18 hours. The solvent was removed under reduced pressure and the residue was partitioned between CH₂Cl₂ (10 mL) and 4% aqueous HCl (10 mL). The organic phase was then extracted with water (10 mL), saturated aqueous sodium bicarbonate solution, and brine. The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent removed under reduced pressure to afford a white foam. The foam was rechromatographed on a preparative HPLC using a gradient of 95:5 to 5:95 water:acetonitrile (0.1%TFA added). The appropriate fractions were combined and freeze dried giving the title compound as a lyophilized solid.

Analysis calculated for (C₃₀H₃₀N₂O₅.0.10 CH₂Cl₂, 0.35 HCl) C, 69.54; H, 5.92; N, 5.39 Found C, 69.55; H, 6.02; N, 5.42

TLC: R_f=0.75 in [10% MeOH(NH₃)/90% CH₂Cl₂]

HPLC (method A): retention time 10.32 min.

FAB MS: m/z 499 (M⁺+H)

EXAMPLE 5

1-{1-[4-(3-azabicyclo-[3.3.0]-octanyl-7-oxy)-2-methoxybenzoyl]-piperidin-4-yl}-4H-3,1-benzoxazin-2(1H)-one

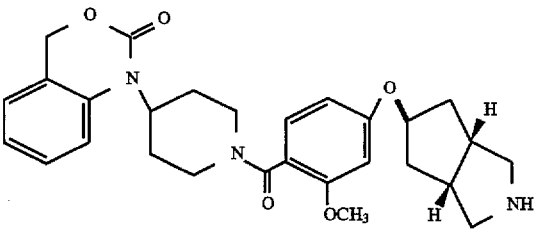

A stirred solution of the compound of EXAMPLE 3 (370 mg, 0.62 mmol) in EtOAc (7 mL) was cooled to 0° C. Anhydrous HCl was bubbled into the cooled solution for 5 minutes and the reaction was warmed to ambient temperature. The solvent was removed under reduced pressure to afford the title compound as a foam. The product was dissolved in 9:1 acetonitrile: water and freeze dried giving the title compound as a lyophilized solid.

Analysis calculated for (C₂₈H₃₃N₃O₅.0.05 HCl, 1.90 H₂O) C, 59.85; H, 6.28; N, 7.48 Found C, 59.84; H, 6.18; N, 7.48

TLC: R_f=0.20 [20% MeOH(NH₃)/80% CH₂Cl₂]

HPLC (method A): retention time 6.31 min.

FAB MS: m/z 492 (M⁺+H)

EXAMPLE 6

(±)-1-{1-[4-(1,2,3,4-tetrahydronaphthyl-1-oxy)-2-methoxybenzoyl]-piperidin-4-yl}-4H-3,1-benzoxazin-2(1H)-one

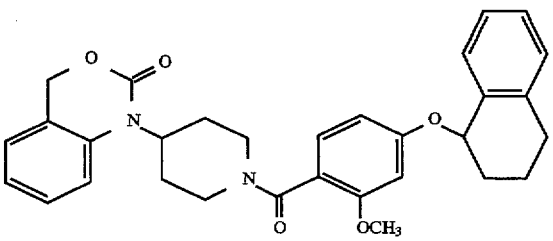

Step 1. To a stirred solution of methyl 4-hydroxy-2-methoxybenzoate (368 mg, 2.03 mmol) in dry THF (1.25 mL) was added triphenylphosphine (425 mg, 1.62 mmol)

and the solution was cooled to 0° C. A 500 mL volume of tetrahydro-1-naphthol (183 mL, 1.35 mmol) and diethyl azodicarboxylate (319 µL, 2.02 mmol) in THF was added dropwise via syringe over 0.5 h. The reaction was filtered and the solvent was removed under reduced pressure. The residue was chromatographed on a silica gel column packed in 90:10 hexanes:EtOAc and eluted with same. The appropriate fractions were combined and the solvent removed under reduced pressure to afford methyl 4-(1-tetrahydronaphthol)-2-methoxybenzoate.

Step 2. To a stirred solution of methyl 4-(1-tetrahydronaphthol)-2-methoxybenzoate (270 mg, 0.86 mmol) in THF:H$_2$O (2 mL: 0.4 mL) was added LiOH.H$_2$O (72.6 mg, 1.73 mmol). The reaction was heated to 45° C. over 12 h and then cooled to ambient temperature. The solvent was removed under reduced pressure. The crude solid was passed through a small plug of silica gel packed in 80:20 hexanes:EtOAc and eluted with 50:50 hexanes:EtOAc. The solvent was removed under reduced pressure to afford 4-(1-tetrahydronaphthol)-2-methoxy-benzoic acid as a foam.

Step 3. To a stirred solution of 4-(1-indanoyloxy)-2-methoxy-benzoic acid (80 mg, 0.27 mmol) in DMF (3.5 mL) was added EDC (61.7 mg, 0.32 mmol), HOBT (49.3 mg, 0.32 mmol) and then 1-(4-piperidinyl)-1,2-dihydro-4(H)-3,1-benzoxazin-2-one (75 mg, 0.32 mmol). The pH of the solution was adjusted to 8.5 (wetted E. Merck pH sticks) using diisopropylethylamine. The solution was stirred for 16 hours. The solvent was removed under reduced pressure and the residue was partitioned between CH$_2$Cl$_2$ (10 mL) and 4% aqueous HCl (10 mL). The organic phase was then extracted with water (10 mL), saturated aqueous sodium bicarbonate solution, and brine. The organic phase was dried (MgSO$_4$), filtered and the solvent was removed under reduced pressure. The residue was chromatographed on a silica gel column packed in 99:1 CH$_2$Cl$_2$:MeOH and eluted with same. The appropriate fractions were combined and the solvent removed under reduced pressure to afford a white foam. The foam was rechromatographed on a preparative HPLC using a gradient of 95:5 to 5:95 water:acetonitrile (0.1%TFA added). The appropriate fractions were combined and freeze dried giving the title compound as a lyophilized solid.

Analysis calculated for (C$_{31}$H$_{32}$N$_2$O$_5$.0.30 CH$_3$CN, 1.0 H$_2$O) C, 69.90; H, 6.48; N, 5.93 Found C, 69.88; H, 6.24; N, 5.97

TLC: R$_f$=0.80 [10% MeOH(NH$_3$)/90% CH$_2$Cl$_2$]

HPLC (method A): retention time 10.86 min.

FAB MS: m/z 513 (M$^+$+H)

EXAMPLE 7

1-{1-[4-(cis-2-phenyl-1-cyclohexanyloxy)-2-methoxybenzoyl]-piperidin-4-yl}-4H-3,1-benzoxazin-2(1H)-one

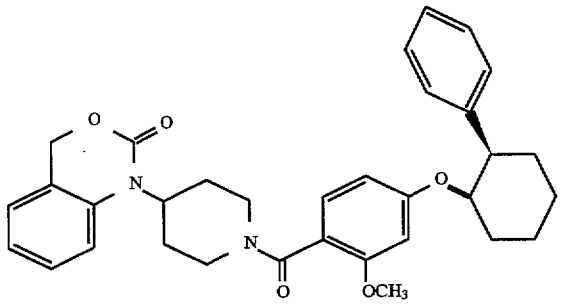

Step 1. To a stirred solution of methyl 4-hydroxy-2-methoxybenzoate (310 mg, 1.7 mmol) in dry THF (1.25 mL) was added triphenylphosphine (446 mg, 1.7 mmol) and the solution was cooled to 0° C. A 500 mL volume of trans-2-phenyl-1-cyclohexanol (200 mg, 1.35 mmol) and diethyl azodicarboxylate (319 µL, 2.02 mmol) in THF was added dropwise via addition funnel over 0.5 h. The reaction was filtered and the solvent was removed under reduced pressure. The residue was chromatographed on a silica gel column packed in 92:8 hexanes:EtOAc and eluted with same. The appropriate fractions were combined and the solvent removed under reduced pressure to afford methyl 4-(cis-2-phenyl-1-cyclohexanoyloxy)-2-methoxybenzoate.

Step 2. To a stirred solution of methyl 4-(cis-2-phenyl-1-cyclohexanoyloxy)-2-methoxybenzoate (230 mg, 0.64 mmol) in THF:H$_2$O (5 mL:1 mL) was added LiOH.H$_2$O (113.5 mg, 2.7 mmol). The reaction was heated to 45° C. over 12 h and then cooled to ambient temperature. The solvent was removed under reduced pressure. The crude solid was passed through a small plug of silca gel packed in 90:10 CH$_2$Cl$_2$:MeOH(NH$_3$) and eluted with same. The solvent was removed under reduced pressure to afford 4-(cis-2-phenyl-1-cyclohexanoyloxy)-2-methoxy-benzoic acid as a foam.

Step 3. To a stirred solution of 4-(cis-2-phenyl-1-cyclohexanoyloxy)-2-methoxybenzoic acid (130 mg, 0.40 mmol) in DMF (3.0 mL) was added EDC (91.6 mg, 0.48 mmol), HOBT (73.1 mg, 0.48 mmol) and then 1-(4-piperidinyl)-1,2-dihydro-4(H)-3,1-benzoxazin-2-one (111 mg, 0.48 mmol). The pH of the solution was adjusted to 8.5 (wetted E. Merck pH sticks) using diisopropylethylamine. The solution was stirred for 16 hours. The solvent was removed under reduced pressure and the residue was partitioned between CH$_2$Cl$_2$ (10 mL) and 4% aqueous HCl (10 mL). The organic phase was then extracted with water (10 mL), saturated aqueous sodium bicarbonate solution, and brine. The organic phase was dried (MgSO$_4$), filtered and the solvent was removed under reduced pressure. The residue was chromatographed on a silica gel column packed in 99:1 CH$_2$Cl$_2$:MeOH and eluted with same. The appropriate fractions were combined and the solvent removed under reduced pressure to afford a white foam. The foam was dissolved in 95:5 water:acetonitrile and freeze dried to give the title compound as a lyophilized solid.

Analysis calculated for (C$_{33}$H$_{36}$N$_2$O$_5$.0.15 H$_2$O, 0.65 CH$_3$CN) C, 72.26; H, 6.76; N, 6.51 Found C, 72.25; H, 6.66; N, 6.44

TLC: R$_f$=0.75 in [10% MeOH(NH$_3$)/90% CH$_2$Cl$_2$]

HPLC (method A): retention time 11.97 min.
FAB MS: m/z 541 (M⁺+H)

EXAMPLE 8

1-{1-[4-{N-acetyl-3-azabicyclo-[3.3.0]-octanyl-7-oxy})-2-methoxybenzoyl]-piperidin-4-yl}-4H-3,1-benzoxazin-2(1H)-one

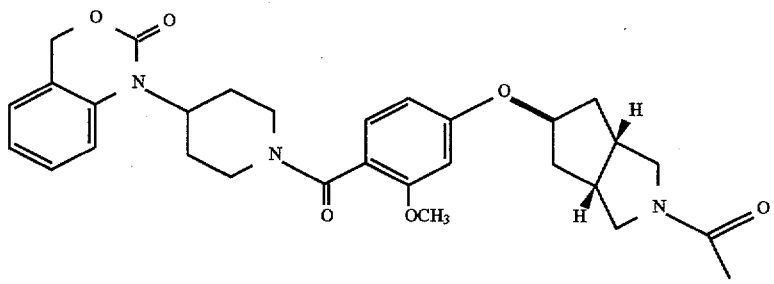

To a stirred solution of the compound of EXAMPLE 5 (150 mg, 0.305 mmol) in $CH_2Cl_2$ (3 mL) was added acetic anhydride (35 μL, 0.37 mmol) and diisopropylethylamine (106 mL, 0.61 mmol). The reaction was stirred for 12 h and the solvent removed under reduced pressure. The residue was chromatographed on a silica gel column packed in 98:2 $CH_2Cl_2$:MeOH($NH_3$) and eluted with same. The appropriate fractions were combined and the solvent was removed under reduced pressure to give an oil which was dissolved in 9:1 acetonitrile:water and freeze dried giving the title compound as a lyophilized solid.

Analysis calculated for ($C_{30}H_{35}N_3O_6 \cdot 0.05$ $CH_3CN$, 0.70 $H_2O$ ) C, 65.93; H, 6.72; N, 7.79 Found C, 65.93; H, 6.53; N, 7.83

TLC: $R_f$=0.80 [10% MeOH($NH_3$)/90% $CH_2Cl_2$]
HPLC (method A): retention time 7.40 min.
FAB MS: m/z 534 (M⁺+H)

EXAMPLE 9

1-{1-[4-(3-{N-oxo-2-ethyl-3-pyridylmethyl}-3-azabicyclo-[3.3.0]-octanyl-7-oxy)-2-methoxybenzoyl]-piperidin-4-yl}-4H-3,1-benzoxazin-2(1H )-one

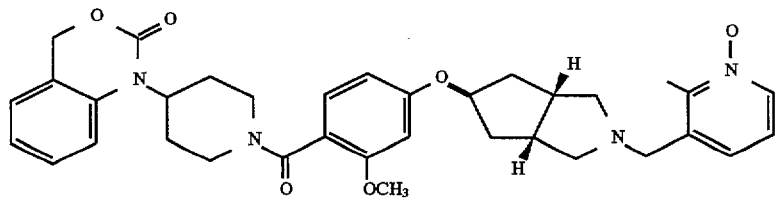

Step 1: To a stirred solution of ethyl 2-methylnicotinate (1.50 g, 9.09 mmol) in freshly distilled THF (100 mL) at 0° C. was added diisobutylaluminum hydride (11.2 mL of a 1.5M solution in toluene, 16.9 mmol). The solution was stirred for 6 h at 0° C. and then warmed to ambient temperature. After 1 h, the solution was cooled in an ice bath and 1N HCl (75 mL) was added to quench the reaction. The mixture was made alkaline with aqueous NaOH (pH=8.5), filtered, and the solvents were concentrated under reduced pressure. The resulting aqueous solution was partitioned between $CHCl_3$ and saturated aqueous $NaHCO_3$. The organic layer was separated, and the aqueous layer was washed with additional $CHCl_3$ (5×40 mL). The organic layers were combined, dried ($MgSO_4$), and evaporated under reduced pressure. 3-Hydroxymethyl-2-methylpyridine was obtained as a slightly amber oil and was used in the next step without purification (TLC: $R_f$=0.40 (5% MeOH:$CH_2Cl_2$)).

Step 2: To a stirred solution of 3-hydroxymethyl-2-methylpyridine from Step 1 above (1.00 g, 8.13 mmol) in 40 mL of $CH_2Cl_2$ at ambient temperature was added $SOCl_2$ (9.0 mL, 123 mmol). The reaction mixture was stirred for 4 hours, and the solvent and excess $SOCl_2$ were evaporated under reduced pressure. The residue was partitioned between $CH_2Cl_2$ and saturated aqueous $NaHCO_3$. The organic layer was separated, and the aqueous layer was washed with additional $CH_2Cl_2$ (2×40 mL). The combined organic layers were evaporated under reduced pressure to give 3-chloromethyl-2-methylpyridine as a pale yellow-brown solid (TLC: $R_f$=0.85 in 5% MeOH in $CH_2Cl_2$; FAB MS m/z 142 (M⁺+H)).

Step 3: To a stirred solution of 3-chloromethyl-2-methylpyridine from Step 2 above (0.50 g; 3.5 mmol) in $CHCl_3$ (40 mL) was added m-chloroperoxybenzoic acid (1.1 g of 55:45 mCPBA:mCBA; 3.5 mmol). After 1.5 h, TLC analysis indicated complete conversion to a lower $R_f$ product. The solution was extracted with equal volumes of saturated aqueous $NaHCO_3$ and water, dried ($MgSO_4$), filtered, and evaporated under reduced pressure. The residue was purified by pressurized silica gel column chromatography using 97:3 $CH_2Cl_2$:MeOH as eluant. 3-Chloromethyl-2-methylpyridine N-oxide was obtained as a solid (TLC: $R_f$=0.30 (97:3 $CH_2Cl_2$:MeOH); FAB MS m/z 158 (M⁺+H)).

Step 4: To a stirred solution of the compound of EXAMPLE 5 (120 mg, 0.24 mmol) in $CH_2Cl_2$ (3 mL) was added 3-chloromethyl- 2-methylpyridine-N-oxide from Step 3 above (79 mg, 0.41 mmol) and diisopropylethylamine (209 μL, 1.20 mmol). The reaction was stirred for 48 h and then the solvent removed under reduced pressure to give a crude oil. The residue was chromatographed on a silica gel column packed in 98:2 $CH_2Cl_2$:MeOH($NH_3$) and eluted with same. The appropriate fractions were combined and the solvent was removed under reduced pressure to give an oil

27 which was dissolved in 9:1 acetonitrile:water and freeze dried giving the title compound as a lyophilized solid.

Analysis calculated for $(C_{35}H_{40}N_4O_6 \cdot 0.35\ CH_3CN, 2.45\ H_2O)$ C, 63.88; H, 6.90; N, 9.08 Found C, 63.88; H, 6.81; N, 9.04

TLC: $R_f$=0.65 [10% MeOH(NH$_3$)/90% CH$_2$Cl$_2$]
HPLC (method A): retention time 6.24 min.
FAB MS: m/z 613 (M$^+$+H)

EXAMPLE 10

(±)-1-{1-[4-(chromanyl-4-oxy)-2-methoxybenzoyl]-piperidin-4-yl}-4H-3,1-benzoxazin-2(1H)-one

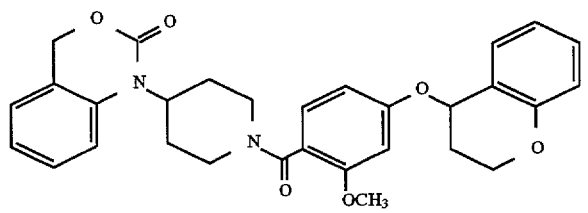

Step 1. To a stirred solution of methyl 4-hydroxy-2-methoxybenzoate (364 mg, 2.0 mmol) in dry THF (1.25 mL) was added triphenylphosphine (525 mg, 2.0 mmol) and the solution was cooled to 0° C. A 500 mL volume of 4-chromanol (200 mg, 1.33 mmol) and diethyl azodicarboxylate (315 mL, 2.0 mmol) in THF was added dropwise via syringe over 0.5 h. The reaction was filtered and the solvent was removed under reduced pressure. The residue was chromatographed on a silica gel column packed in 92:8 hexanes:EtOAc and eluted with same. The appropriate fractions were combined and the solvent removed under reduced pressure to afford methyl 4-(4-chromanoyloxy)-2-methoxybenzoate.

Step 2. To a stirred solution of methyl 4-(4-chromanoyloxy)-2-methoxybenzoate (260 mg, 0.82 mmol) in THF:H$_2$O (4 mL:0.8 mL) was added LiOH.H$_2$O (172 mg, 4.1 mmol). The reaction was heated to 45° C. over 12 h and then cooled to ambient temperature. The solvent was removed under reduced pressure. The crude solid was passed through a small plug of silca gel packed in 90:10 CH$_2$Cl$_2$:MeOH(NH$_3$) and eluted with same. The solvent was removed under reduced pressure to afford 4-(4-chromanoyloxy)-2-methoxybenzoic acid as a foam.

Step 3. To a stirred solution of 4-(4-chromanoyloxy)-2-methoxybenzoic acid (50 mg, 0.17 mmol) in DMF (1.0 mL) was added EDC (38.3 mg, 0.20 mmol), HOBT (30.6 mg, 0.20 mmol) and then 1-(4-piperidinyl)-1,2-dihydro-4(H)-3,1-benzoxazin-2-one (46.4 mg, 0.20 mmol). The pH of the solution was adjusted to 8.5 (wetted E. Merck pH sticks) using diisopropylethylamine. The solution was stirred for 16 hours. The solvent was removed under reduced pressure and the residue was partitioned between CH$_2$Cl$_2$ (5 mL) and 4% aqueous HCl (5 mL). The organic phase was then extracted with water (5 mL), saturated aqueous sodium bicarbonate solution, and brine. The organic phase was dried (MgSO$_4$), filtered and the solvent was removed under reduced pressure. The residue was chromatographed on a silica gel column packed in 99.5:0.5 CH$_2$Cl$_2$:MeOH and eluted with same. The appropriate fractions were combined and the solvent removed under reduced pressure to afford a white foam. The foam was dissolved in 95:5 water: acetonitrile and freeze dried to give the title compound as a lyophilized solid.

28

Analysis calculated for $(C_{30}H_{30}N_2O_6 \cdot 0.05\ CH_3CN, 1.55\ H_2O)$ C, 66.33; H, 6.15; N, 5.27 Found C, 66.35; H, 5.98; N, 5.31

TLC: $R_f$=0.80 [10% MeOH(NH$_3$)/90% CH$_2$Cl$_2$]
HPLC (method A): retention time 9.87 min.
FAB MS: m/z 515 (M$^+$+H)

EXAMPLE 11

(±)-1-{1-[4-(5,6,7,8-tetrahydro-3,7,7-trimethylquinoline-5-oxy)-2-methoxybenzoyl]-piperidin-4-yl}-4H-3,1-benzoxazin-2(1H)-one

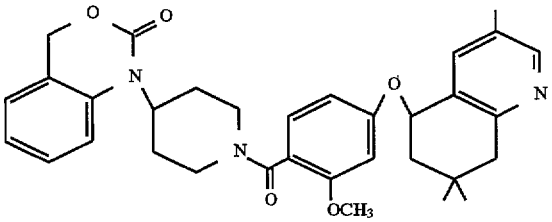

Step 1. A stirred solution of 5,6,7,8-tetrahydro-3,7,7-trimethylquinoline-5-one (240 mg, 1.3 mmol) in MeOH (6.5 mL) was cooled to 0° C. under Argon and treated with NaBH$_4$ (48 mg, 1.3 mmol). The reaction was stirred over 14 h and allowed to warm to ambient temperature. The solvent was removed under reduced pressure and the crude oil that was chromatographed on a silica gel column packed in 95:5 EtOAc:hexanes and eluted with same. The appropriate fractions were combined and the solvent was removed under reduced pressure to give 5,6,7,8-tetrahydro-3,7,7-trimethylquinoline-5-ol.

Step 2. To a stirred solution of methyl 4-hydroxy-2-methoxybenzoate (213.5 mg, 1.2 mmol) in dry THF (1.5 mL) was added triphenylphosphine (308 mg, 1.2 mmol) and the solution was cooled to 0° C. A 1 mL volume of 5,6,7,8-tetrahydro-3,7,7-trimethylquinoline-5-ol (146 mg, 0.76 mmol) and diethyl azodicarboxylate (185 μL, 1.2 mmol) in THF was added dropwise via addition funnel over 0.25 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-[5-(5,6,7,8-tetrahdro-3,7,7-trimethylquinoline)oyloxy]-2-methoxybenzoate.

Step 3. To a stirred solution of methyl 4-[5-(5,6,7,8-tetrahydro-3,7,7-trimethylquinoline)oyloxy]-2-methoxybenzoate (55 mg, 0.15 mmol) in THF:H$_2$O (0.5 mL: 0.1 mL) was added LiOH.H$_2$O (11.8 mg, 0.28 mmol). The reaction was heated to 45° C. over 12 h and then cooled to ambient temperature. The solvent was removed under reduced pressure. The crude solid was chromatographed on a silica gel column packed in in 80:20 hexanes:EtOAc and eluted with same. The solvent was removed under reduced pressure to afford 4-[5-(5,6,7,8-tetrahydro-3,7,7-trimethylquinoline)oyloxy]-2-methoxybenzoic acid as a foam.

Step 4. To a stirred solution of 4-[5-(5,6,7,8-tetrahydro-3,7,7-trimethylquinoline)oyloxy]-2-methoxybenzoic acid (20 mg, 0.06 mmol) in DMF (1 mL) was added EDC (13.8 mg, 0.07 mmol), HOBT (11 mg, 0.07 mmol) and then 1-(4-piperidinyl)-1,2-dihydro-4(H)-3,1-benzoxazin-2-one (16.7 mg, 0.07 mmol). The pH of the solution was adjusted to 8.5 (wetted E. Merck pH sticks) using diisopropylethylamine. The solution was stirred for 18 hours. The solvent was removed under reduced pressure and the residue was partitioned between CH₂Cl₂ (5 mL) and 4% aqueous HCl (5 mL). The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for ($C_{33}H_{37}N_3O_5 \cdot 1.20$ $CH_2Cl_2$, 0.15 $CH_3CN$) C, 68.55; H, 6.88; N, 7.56 Found C, 68.56; H, 6.55; N, 7.53

TLC: $R_f$=0.85 [10% MeOH($NH_3$)/90% $CH_2Cl_2$]

HPLC (method A): retention time 7.39 min.

FAB MS: m/z 556 ($M^+$+H)

EXAMPLE 12

1-{1-[4-(N-oxo-2-ethyl-3-pyridylmethoxy)-2-methoxybenzoyl]-piperidin-4-yl}-4H-3,1-benzoxazin-2(1H)-one

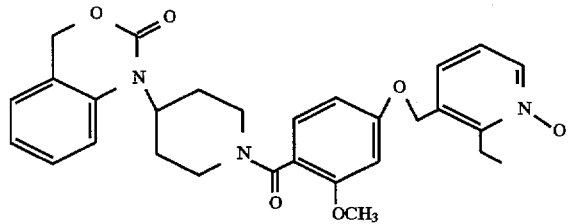

Step 1. A quantity of 2-methyl nicotinic acid was prepared following the procedure cited in Breitmaier et al, *Tetrahedron* 26 (24), 5907–12 (1970).

Step 2. A solution of LDA was prepared by adding butyl lithium (1.6M in hexanes) (4.79 mL, 7.67 mmol) dropwise with stirring to freshly distilled diisopropylamine (1.07 mL, 7.67 mmol) in THF (15 mL) under nitrogen at –20° C. The resulting solution was transferred by cannula into a cold (–78° C.), stirred solution of 2-methyl nicotinic acid (500 mg, 3.65 mmol) in THF (25 mL) under nitrogen. The reaction was stirred at –78° C. for 30 minutes then warmed to 0° C. for 30 minutes and then cooled to –78° C. Methyl iodide (477 mL, 7.67 mmol) was added and the reaction stirred for 30 minutes, then allowed to warm to ambient temperature and stirred for 3 hours. The product precipitated out of the reaction mixture and was filtered and dried under reduced pressure to give the desired 2-ethyl nicotinic acid as the lithium salt.

Step 3. The 2-ethyl nicotinic acid lithium salt (5 g, 3.18 mmol) in distilled THF (400 mL) under nitrogen was cooled to 0° C. and lithium aluminum hydride (1M in THF) (25 mL) was added dropwise. The reaction was stirred for 3 hours at room temperature then cooled to 0° C. and quenched with EtOAc (949 μL), then H₂O (949 μL), then 15% NaOH (949 μL), followed by H₂O (2.8 mL). The solution was filtered and the solvent was removed under reduced pressure. Toluene was added and the solvent was removed under reduced pressure to give the desired 2-ethyl-3-hydroxymethylpyridine.

Step 4. The 2-ethyl-3-hydroxymethylpyridine (2.3 g, 16.8 mmol) was dissolved in CH₂Cl₂ (100 mL) and cooled under nitrogen to 0° C. and thionyl chloride (7.0 mL) was slowly added and the reaction was stirred for 3 hours. The solvent was removed under reduced pressure and the residue was partitioned between CH₂Cl₂ (100 mL) and saturated aqueous sodium bicarbonate (100 mL). The organic layer was dried with MgSO₄, filtered, and the solvent removed under reduced pressure to give the desired 2-ethyl-3-chloromethylpyridine.

Step 5. The 2-ethyl-3-chloromethylpyridine (2.4 g, 15.4 mmol) was dissolved in CHCl₃ (100 mL) and cooled under nitrogen to 0° C. and m-chloroperbenzoic acid (55%, 4.2 g) was added in small portions. The reaction was stirred for 2 hours. The reaction was extracted twice with saturated aqueous sodium bicarbonate (100 mL). The organic phase was dried with MgSO₄, filtered and the solvent was removed under reduced pressure. The residue was chromatographed on silica gel packed in 98:2 CH₂Cl₂:MeOH and eluted with the same. The appropriate fractions were combined and the solvent removed under reduced pressure the give the desired 2-ethyl-3-chloromethylpyridine-N-oxide.

Step 6. To a stirred solution of Compound A (200 mg, 0.52 mmol) in dry DMF (10 mL) was added cesium carbonate (1.5 g, 5.2 mmol) followed by 2-ethyl-3-chloromethylpyridine-N-oxide (160 mg, 1.04 mmol) and the reaction was warmed to 50° C. under argon and stirred for 18 hours. The reaction was filtered and the solvent was removed under reduced pressure. The residue was partitioned between CH₂Cl₂ (100 mL) and 4% aqueous HCL (100 mL). The organic layer was extracted with saturated sodium bicarbonate solution (100 mL), water, and brine and dried with MgSO₄ and filtered. The solvent was removed under reduced pressure to give a foam which was chromatographed on a silica gel column packed in 98:2 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for ($C_{29}H_{31}N_3O_6 \cdot 0.75$ $H_2O$) C, 65.58; H, 6.17; N, 7.91 Found C, 65.54; H, 5.98; N, 7.95

TLC: $R_f$=0.4 in 10% MeOH/90% $CH_2Cl_2$

HPLC (method A): retention time 8.04 min.

FAB MS: m/z 518 ($M^+$+H)

EXAMPLE 13

1-{1-[4-(N-oxo-2-isopropyl-3-pyridylmethoxy)-2-methoxybenzoyl]-piperidin-4-yl}-4H-3,1-benzoxazin-2(1H)-one

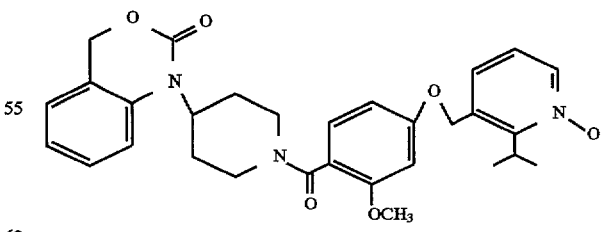

Step 1. A quantity of 2-isopropyl-3-carboethoxypyridine was prepared following the procedure cited in Breitmaier et al, *Tetrahedron* 26 (24), 5907–12 (1970).

Step 2. The 2-isopropyl-3-carboethoxypyridine (400 mg, 2 mmol) in distilled THF (50 mL) under nitrogen was cooled to 0° C. and lithium aluminum hydride (1M in THF) (2.07 mL) was added dropwise. The reaction was stirred for 18 hours at room temperature then cooled to 0° C. and quenched with EtOAc (100 μL), then H₂O (100 μL), then 15% NaOH (100 μL), followed by H₂O (300 μL). The mixture was filtered and the solvent was removed under reduced pressure. Toluene was added and the solvent was removed under reduced pressure to give the desired 2-isopropyl-3-hydroxymethylpyridine.

Step 3. The 2-isopropyl-3-hydroxymethylpyridine (240 mg, 1.59 mmol) was dissolved in CH₂Cl₂ (15 mL) and cooled under nitrogen to 0° C. and thionyl chloride (1.0 mL) was slowly added and the reaction was stirred for 3 hours. The solvent was removed under reduced pressure and the residue was partitioned between CH₂Cl₂ and saturated sodium bicarbonate. The organic layer was dried with MgSO₄, filtered and the solvent removed under reduced pressure to give the desired 2-isopropyl-3-chloromethylpyridine. The 2-isopropyl-3-chloromethylpyridine (65 mg, 0.383 mmol) was dissolved in CHCl₃ (10 mL) and cooled under nitrogen to 0° C. and m-chloroperbenzoic acid (55%, 150 mg) was added in small portions. The reaction was stirred for 2 hours. The solution was extracted with saturated aqueous sodium bicarbonate (2×5 mL). The organic phase was dried with MgSO₄, filtered, and the solvent removed under reduced pressure. The residue was chromatographed on silica gel packed in 99:1 CH₂Cl₂:MeOH and eluted with same. The appropriate fractions were combined and the solvent removed under reduced pressure to give the desired 2-isopropyl-3-chloromethylpyridine-N-oxide.

Step 4. To a stirred solution of Compound A (200 mg, 0.52 mmol) in dry DMF (10 mL) was added cesium carbonate (1.5 g, 5.2 mmol) followed by 2-isopropyl-3-chloromethylpyridine N-oxide (175 mg, 1.04 mmol) and the reaction was warmed to 50° C. under argon and stirred for 18 hours. The reaction was filtered and the solvent was removed under reduced pressure. The residue was partitioned between CH₂Cl₂ (100 mL) and 4% aqueous HCL (100 mL). The organic layer was extracted with saturated aqueous sodium bicarbonate solution (100 mL), water, and brine, then dried over MgSO₄ and filtered. The solvent was removed under reduced pressure to give a foam which was chromatographed on a silica gel column packed in 98:2 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C₃₀H₃₃N₃O₆·0.70 H₂O) C, 66.20; H, 6.37; N, 7.72 Found C, 66.15; H, 6.20; N, 7.65

TLC: R_f=0.35 in 5% MeOH/95% CH₂Cl₂

HPLC (method A): retention time 8.51 min.

FAB MS: m/z 532 (M⁺+H)

EXAMPLE 14

1-{1-[4-(N-oxo-2,4-dimethyl-3-pyridylmethoxy)-2-methoxybenzoyl]-piperidin-4-yl}-4H-3,1-benzoxazin-2(1H)-one

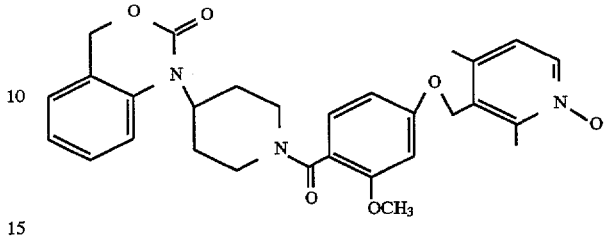

Step 1. Preparation of 2,4-dimethyl-3-carboethoxypyridine was carried out as described in Ohno et al, J. Am. Chem. Soc. 101, 7036–7040 (1979).

Step 2. The 2,4-dimethyl-3-carboethoxypyridine (11.3 g, 63.1 mmol) in distilled THF (375 mL) under nitrogen was cooled to 0° C. and lithium aluminum hydride (1M in THF, 63.1 mL) was added dropwise. The reaction was stirred for 18 hours at room temperature then cooled to 0° C. and quenched with EtOAc (2.5 mL), then H₂O (2.5 mL), then 15% NaOH (2.5 mL), followed by H₂O (7.5 mL). The solution was filtered and the solvent removed under reduced pressure to give the desired 2,4-dimethyl-3-hydroxymethylpyridine.

Step 3. The 2,4-dimethyl-3-hydroxymethylpyridine (19.2 g, 140 mmol) was dissolved in CH₂Cl₂ (800 mL) and cooled under nitrogen to 0° C. and thionyl chloride (125 mL) was slowly added and the reaction was stirred for 18 hours. The solvent was removed under reduced pressure and the residue was partitioned between CH₂Cl₂ and saturated aqueous sodium bicarbonate. The organic layer was dried with MgSO₄, filtered and the solvent removed under reduced pressure to give the desired 2,4-dimethyl-3-chloromethylpyridine.

Step 4. The 2,4-dimethyl-3-chloromethylpyridine (21.5 g, 138 mmol) was dissolved in CHCl₃ (800 mL) and cooled under nitrogen to 0° C. and m-chloroperbenzoic acid (55%, 35 g) was added in small portions. The reaction was stirred for 4 hours. The solution was extracted twice with saturated aqueous sodium bicarbonate (500 mL). The organic phase was dried with MgSO₄, filtered and the solvent removed under reduced pressure. The residue was chromatographed on silica gel packed in 98:2 CH₂Cl₂:MeOH and eluted with same. The appropriate fractions were combined and the solvent was removed under reduced pressure the give the desired 2,4-dimethyl-3-chloromethylpyridine-N-oxide.

Step 5. To a stirred solution of Compound A (200 mg, 0.52 mmol) in dry DMF (10 mL) was added cesium carbonate (1.5 g, 5.2 mmol) followed by 2,4-dimethyl-3-chloromethylpyridine-N-oxide (160 mg, 1.04 mmol) and the reaction was warmed to 50° C. under argon and stirred for 18 hours. The mixture was filtered and the solvent was removed under reduced pressure. The residue was partitioned between CH₂Cl₂ (100 mL) and 4% aqueous HCL (100 mL). The organic layer was washed with saturated aqueous sodium bicarbonate (100 mL), water, and brine and dried with MgSO₄ and filtered. The solvent was removed under reduced pressure to give a foam which was chromatographed on a silica gel column packed in 96:4 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{29}$H$_{31}$N$_3$O$_6$.1.90 H$_2$O) C, 63.11; H, 6.36; N, 7.62 Found C, 63.12; H, 5.80; N, 7.64

TLC: R$_f$=0.25 in 5% MeOH/95% CH$_2$Cl$_2$

HPLC (method A): retention time 7.75 min.

FAB MS: m/z 518 (M$^+$+H)

EXAMPLE 15

(±)-1-{1-[4-{5,6,7,8-tetrahydroquinoline-5-oxy}}-2-methoxybenzoyl]-piperidin-4-yl}-4H-3,1-benzoxazin-2(1H)-one

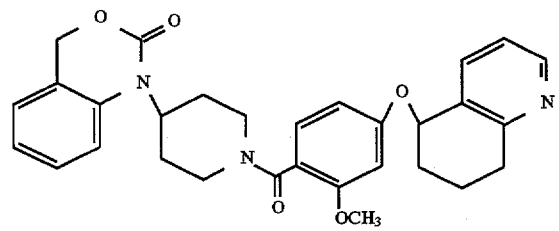

A quantity of (5,6,7,8)-tetrahydroquinoline-5-one was prepared following the procedure cited in Zymalkowski, F.; Rimek, H. *Arch. Pharm.* 1961, 294, 759–765.

Step 1. A stirred solution of (5,6,7,8)-tetrahydroquinoline-5-one (500 mg, 3.4 mmol) in MeOH (17 mL) was cooled to 0° C. under Argon and treated with NaBH$_4$ (128.7 mg, 3.4 mmol). The reaction was stirred over 16 h and allowed to warm to ambient temperature. The solvent was removed under reduced pressure and the crude oil was chromatographed on a silica gel column packed in 95:5 EtOAc:hexanes and eluted with same. The appropriate fractions were combined and the solvent was removed under reduced pressure to give the 5-hydroxy-(5,6,7,8)-tetrahydroquinoline.

Step 2. To a stirred solution of methyl 4-hydroxy-2-methoxybenzoate (928.2 mg, 5.1 mmol) in dry THF (3 mL) was added triphenylphosphine (1.34 g, 5.1 mmol) and the solution was cooled to 0° C. A 2 mL volume of 5-hydroxy-(5,6,7,g)-tetrahydroquinoline (500 mg, 3.4 mmol) and diethyl azodicarboxylate (803 µL, 5.1 mmol) in THF was added dropwise via addition funnel over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-[5-(5,6,7,8)-tetrahydroquinolinoyloxy]-2-methoxybenzoate.

Step 3. To a stirred solution of methyl 4-[5-(5,6,7,8)-tetrahydroquinolinoyloxy]-2-methoxybenzoate (720 mg, 2.3 mmol) in THF:H$_2$O (7 mL: 1.4 mL) was added LiOH.H$_2$O (193 mg, 4.6 mmol). The reaction was heated to 45° C. over 12 h and then cooled to ambient temperature. The solvent was removed under reduced pressure. The crude solid was passed through a plug of silca gel packed in 80:20 hexanes:EtOAc and eluted with same. The solvent was removed under reduced pressure to afford 4-[(5,6,7,8)-tetrahydroquinolinoyl-5-oxy]-2-methoxybenzoic acid as a foam.

Step 4. To a stirred solution of 4-[(5,6,7,8)-tetrahydroquinolinoyl-5-oxy]-2-methoxybenzoic acid (150 mg, 0.5 mmol) in DMF (4 mL) was added EDC (115.4 mg, 0.6 mmol), HOBT (91.8 mg, 0.6 mmol) and then 1-(4-piperidinyl)-1,2-dihydro-4(H)-3,1-benzoxazin-2-one (140 mg, 0.6 mmol). The pH of the solution was adjusted to 8.5 (wetted E. Merck pH sticks) using diisopropylethylamine. The solution was stirred for 12 hours. The solvent was removed under reduced pressure and the residue was partitioned between CH$_2$Cl$_2$ (25 mL) and 4% aqueous HCl (20 mL). The organic phase was then extracted with water (20 mL), saturated aqueous sodium bicarbonate solution, and brine. The organic phase was dried (MgSO$_4$), filtered and the solvent was removed under reduced pressure. The residue was chromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{30}$H$_{31}$N$_3$O$_5$.0.80 H$_2$O, 0.10 CH$_3$CN) C, 68.16; H, 6.23; N, 8.16 Found C, 68.20; H, 5.89; N, 8.17

TLC: R$_f$=0.80 [10% MeOH(NH$_3$)/90% CH$_2$Cl$_2$]

HPLC (method A): retention time 6.79 min.

FAB MS: m/z 514 (M$^+$+H)

EXAMPLE 16

1-{1-[4-[cis-4-aminocyclohexyloxy]-2-methoxybenzoyl]-piperidin-4-yl}-4H-3,1-benzoxazin-2(1H)-one

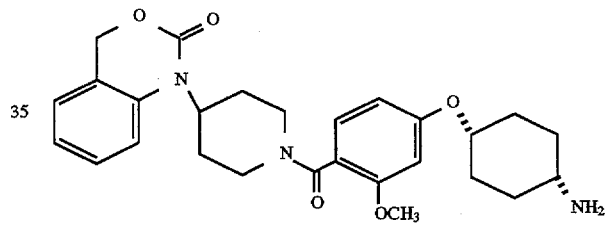

Step 1. A stirred solution of trans-1-amino-4-cyclohexanol (2 g, 13.2 mmol) in CH$_2$Cl$_2$ (26 mL) was cooled to 0° C. under Argon and treated with di-tert-butyl dicarbonate (2.88 g, 13.2 mmol) and triethylamine (4.6 mL, 33 mmol). The solution was allowed to warm to ambient temperature over 16 h and the solvent removed under reduced pressure. The crude product was chromatographed on a silica gel column packed in 70:30 hexanes:EtOAc and eluted with same. The appropriate fractions were combined and the solvent removed under reduced pressure to afford N-Boc-trans-1-amino-4-cyclohexanol (2.5 g, 9.9 mmol)

Step 2. To a stirred solution of methyl 4-hydroxy-2-methoxybenzoate (1.09 g, 6.0 mmol) in dry THF (7 mL) was added triphenylphosphine (1.57 g, 6.0 mmol) and the solution was cooled to 0° C. A 4.0 mL volume of N-Boc-trans-1-amino-4-cyclohexanol (1 g, 4.0 mmol) and diethyl azodicarboxylate (945 µL, 6.0 mmol) in THF was added dropwise via addition funnel over 0.5 h. The reaction was filtered and the solvent was removed under reduced pressure. The residue was chromatographed on a silica gel column packed in 70:30 hexanes:EtOAc and eluted with same. The appropriate fractions were combined and the solvent removed under reduced pressure to afford methyl 4-[N-Boc-cis-1-amino-4-cyclohexanoyloxy]-2-methoxybenzoate.

Step 3. To a stirred solution of methyl 4-[N-Boc-cis-1-amino-4-cyclohexanoyloxy]-2-methoxybenzoate (220 mg, 0.52 mmol) in THF:H₂O (5 mL: 1 mL) was added LiOH.H₂O (67.6 mg, 1.59 mmol). The reaction was heated to 45° C. over 12 h and then cooled to ambient temperature. The solvent was removed under reduced pressure. The crude solid passed through a plug of silca gel packed in 50:50 MeOH:CH₂Cl₂ and eluted with same. The solvent was removed under reduced pressure to afford 4-[N-Boc-cis-1-amino-4-cyclohexanoyloxy]-2-methoxybenzoic acid as a white solid.

Step 4. To a stirred solution of 4-[N-Boc-cis-1-amino-4-cyclohexanoyloxy]-2-methoxybenzoic acid (200 mg, 0.49 mmol) in DMF (2 mL) was added EDC (115.0 mg, 0.6 mmol), HOBT (91.8 mg, 0.6 mmol) and then 1-(4-piperidinyl)-1,2-dihydro-4(H)-3,1-benzoxazin-2-one (139.2 mg, 0.6 mmol). The pH of the solution was adjusted to 8.5 (wetted E. Merck pH sticks) using diisopropylethylamine. The solution was stirred for 16 hours. The solvent was removed under reduced pressure and the residue was partitioned between CH₂Cl₂ (10 mL) and 4% aqueous HCl (5 mL). The organic phase was then extracted with water (5 mL), saturated aqueous sodium bicarbonate solution, and brine. The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent was removed under reduced pressure to give 1-{1-[4-[N-Boc-cis-1-aminocyclohexanoyl-4-oxy]-2-methoxybenzoyl]-piperidin-4-yl}-4H-3,1-benzoxazin-2(1H)-one.

Step 5. To a stirred solution of 1-{1-[4-[N-Boc-cis-1-amino-4-cyclohexanoyloxyl-2-methoxybenzoyl]-piperidin-4-yl}-4H -3,1-benzoxazin-2(1H)-one (150 mg, 0.25 mmol) in MeOH (2 mL) at 0° C. was bubbled in anhydrous HCl for 2 minutes. The solution was allowed to warm to ambient temperature with stirring and then the solvent was removed under reduced pressure. The crude product was chromatographed on a silica gel column packed in 70:30 CH₂Cl₂:MeOH(NH₃) and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C₂₇H₃₃N₃O₅.2.30 HCl) C, 57.54; H, 6.31; N, 7.74 Found C, 57.55; H, 6.20; N, 7.74

TLC: R_f=0.40 [20% MeOH(NH₃)/80% CH₂Cl₂]

HPLC (method A): retention time 6.60 min.

FAB MS: m/z 480 (M⁺+H)

EXAMPLE 17

1-{1-[4-(1,1-dioxothiopyran-4-oxy)-2-methoxybenzoyl]-piperidin-4-yl}-4H-3,1 -benzoxazin-2(1H)-one

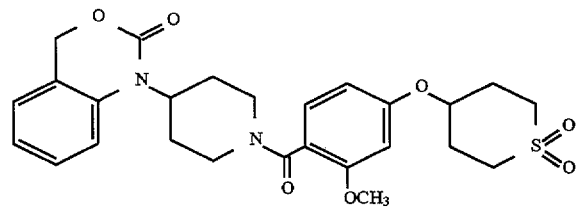

Step 1. A stirred solution of thiopyran-4-one (1 g, 8.6 mmol) in CH₂Cl₂ (10 mL) was cooled to 0° C. under Argon and treated with a solution of peracetic acid (2.5 mL, 40% in acetic acid). The solution was allowed to warm to ambient temperature over 16 h and a white precipitate formed. The solution was filtered through celite and the solvent removed under reduced pressure to afford sulfonylpyran-4-one as a white solid.

Step 2. A stirred solution of sulfonylpyran-4-one (1.2 g, 8.1 mmol) in MeOH (20 mL) was cooled to 0° C. under Argon and treated with NaBH₄ (331 mg, 9.0 mmol). The reaction was stirred over 16 h and allowed to warm to ambient temperature. The solvent was removed under reduced pressure and the crude oil was chromatographed on a silica gel column packed in 50:50 EtOAc:hexanes and eluted with same. The appropriate fractions were combined and the solvent was removed under reduced pressure to give the sulfonylpyran-4-ol.

Step 3. To a stirred solution of methyl 4-hydroxy-2-methoxybenzoate (364 mg, 2.0 mmol) in dry THF (4 mL) was added triphenylphosphine (524.6 mg, 2.0 mmol) and the solution was cooled to 0° C. A 2.5 mL volume of sulfonylpyran-4-ol (200 mg, 1.33 mmol) and diethyl azodicarboxylate (315 µL, 2.0 mmol) in THF was added dropwise via addition funnel over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-[4-sulfonylpyranoyloxy]-2-methoxybenzoate.

Step 4. To a stirred solution of methyl 4-[4-sulfonylpyranoyloxy]-2-methoxybenzoate (470 mg, 1.5 mmol)in THF:H₂O (18 mL: 2 mL) was added LiOH.H₂O (128 mg, 3 mmol). The reaction was heated to 45° C. over 12 h and then cooled to ambient temperature. The solvent was removed under reduced pressure. The crude solid passed through a plug of silca gel packed in 80:20 hexanes:EtOAc and eluted with same. The solvent was removed under reduced pressure to afford 4-[4-sulfonylpyranoyloxy] -2-methoxybenzoic acid as a white solid.

Step 5. To a stirred solution of 4-[4-sulfonylpyranoyloxy] -2-methoxybenzoic acid (130 mg, 0.43 mmol) in DMF (2 mL) was added EDC (99.7 mg, 0.52 mmol), HOBT (79.6 mg, 0.52 mmol) and then 1-(4-piperidinyl)-1,2-dihydro-4 (H)-3,1-benzoxazin-2-one (120.4 mg, 0.52 mmol). The pH of the solution was adjusted to 8.5 (wetted E. Merck pH sticks) using diisopropylethylamine. The solution was stirred for 12 hours. The solvent was removed under reduced pressure and the residue was partitioned between CH₂Cl₂ (5 mL) and 4% aqueous HCl (5 mL). The organic phase was then extracted with water (5 mL), saturated aqueous sodium bicarbonate solution, and brine. The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C₂₆H₃₀N₂O₇S.0.15 HCl, 0.55 CH₂Cl₂) C, 56.66; H, 5.64; N, 4.95 Found C, 56.64; H, 5.64; N, 4.95

TLC: R_f=0.25 [20% MeOH(NH₃)/80% CH₂Cl₂]

HPLC (method A): retention time 7.47 min.

FAB MS: m/z 515 (M⁺+H)

EXAMPLE 18

(±)-1-{1-[4-(1,1-dioxothiochromanyl-4-oxy)-2-methoxybenzoyl]-piperidin-4-yl}-4H-3,1-benzoxazin-2(1H)-one

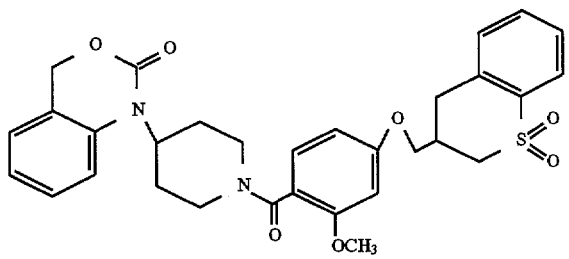

Step 1. A stirred solution of thiochroman-4-ol (1 g, 6.0 mmol) in $CH_2Cl_2$ (10 mL) was cooled to 0° C. under Argon and treated with a solution of peracetic acid (2.5 mL, 40% in acetic acid). The solution was allowed to warm to ambient temperature over 16 h and a white precipitate formed. The solution was filtered through celite and the solvent removed under reduced pressure to afford sulfonylchroman-4-ol as a white solid.

Step 2. To a stirred solution of methyl 4-hydroxy-2-methoxybenzoate (413.1 mg, 2.27 mmol) in dry THF (4.5 mL) was added triphenylphosphine (596.1 mg, 2.27 mmol) and the solution was cooled to 0° C. A 2.5 mL volume of sulfonylchroman-4-ol (300 mg, 1.52 mmol) and diethyl azodicarboxylate (357.5 µL, 2.27 mmol) in THF was added dropwise via addition funnel over 0.5 h. The reaction was filtered and the solvent was removed under reduced pressure. The residue was chromatographed on a silica gel column packed in 70:30 hexanes:EtOAc and eluted with same. The appropriate fractions were combined and the solvent removed under reduced pressure to afford methyl 4-[4-sulfonylchromanoyloxy]-2-methoxybenzoate.

Step 4. To a stirred solution of methyl 4-[4-sulfonylchromanoyloxy]-2-methoxybenzoate (500 mg, 1.38 mmol) in $THF:H_2O$ (18 mL: 2 mL) was added $LiOH.H_2O$ (175 mg, 4.14 mmol). The reaction was heated to 45° C. over 12 h and then cooled to ambient temperature. The solvent was removed under reduced pressure. The crude solid was passed through a plug of silca gel packed in 50:50 $MeOH:CH_2Cl_2$ and eluted with same. The solvent was removed under reduced pressure to afford 4-[4-sulfonylchromanoyloxy]-2-methoxybenzoic acid as a white solid.

Step 5. To a stirred solution of 4-[4-sulfonylchromanoyloxy-2-methoxybenzoic acid (390 mg, 1.12 mmol) in DMF (5 mL) was added EDC (256.9 mg, 1.34 mmol), HOBT (205 mg, 1.34 mmol) and then 1-(4-piperidinyl)-1,2-dihydro-4(H)-3,1-benzoxazin-2-one (312 mg, 1.34 mmol). The pH of the solution was adjusted to 8.5 (wetted E. Merck pH sticks) using diisopropylethylamine. The solution was stirring for 16 hours. The solvent was removed under reduced pressure and the residue was partitioned between $CH_2Cl_2$ (10 mL) and 4% aqueous HCl (5 mL). The organic phase was then extracted with water (5 mL), saturated aqueous sodium bicarbonate solution, and brine. The organic phase was dried ($MgSO_4$), filtered and the solvent was removed under reduced pressure. The residue was chromatographed on a silica gel column packed in 98:2 $CH_2Cl_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{30}H_{30}N_2O_7S.1.45\ CH_2Cl_2, 0.15\ MeOH)$ C, 54.95; H, 4.89; N, 4.06 Found C, 54.95; H, 4.57; N, 4.29

TLC: $R_f$=0.40 [20% $MeOH(NH_3)$/80% $CH_2Cl_2$]

HPLC (method A): retention time 8.58 min.

FAB MS: m/z 563 ($M^+$+H)

EXAMPLE 19

(±)-1-{1-[4-(1-{5-pyrimidinyl}ethoxy)-2-methoxybenzoyl]-piperidin-4-yl}-4H-3,1-benzoxazin-2(1H)-one

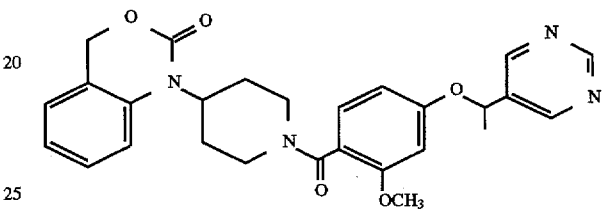

Step 1. A stirred solution of 5-bromopyrimidine (16 g, 0.1 mol) in anhydrous ether (500 mL) and freshly distilled THF (500 mL) was cooled to −110° C. under nitrogen (ether/liquid nitrogen bath). N-butyl lithium (1.6M in hexanes) (94 mL, 1.5 eq) was added over 15 minutes keeping the temperature below −105° C. The mixture was stirred for an additional 15 minutes at −110° C. and acetaldehyde (15 mL, 2 eq) was added via syringe. The mixture was allowed to warm to −60° C. and quenched with 1N HCl (130 mL), allowed to warm to near room temperature and diluted with EtOAc (200 mL). The aqueous layer was saturated with sodium chloride and extracted 5 times with EtOAc (100 mL). The combined organics were dried with $MgSO_4$ and concentrated to a thick oil which was vacuum distilled (1 mm Hg, 120° C.) giving α-methyl-pyrimidylmethanol.

Step 2. To a stirred solution of Compound A (200 mg, 0.52 mmol) in dry THF (10 mL) was added triphenylphosphine (300 mg, 1.15 mmol) and the solution was cooled to 0° C. A 5 mL volume of α-methyl-pyrimidylmethanol (137 mg, 1.15 mmol) and diethyl azodicarboxylate (173 µL, 1.15 mmol) in THF was added dropwise via syringe over 2 hours. The reaction was filtered and the removed under reduced pressure and the residue was chromatographed on a silica gel column packed in 60:40 $CH_2Cl_2$:EtOAc and eluted with same. The appropriate fractions were combined and the solvent was removed under reduced pressure to give an oil which was rechromatographed on a silica gel column packed in 98:2 $CH_2Cl_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{27}H_{28}N_4O_5.1.55\ H_2O)$ C, 62.78; H, 6.07; N, 10.85 Found C, 62.73; H, 5.60; N, 11.18

TLC: $R_f$=0.40 5% MeOH/95% $CH_2Cl_2$

HPLC (method A): retention time 8.23 min.

FAB MS: m/z 489 ($M^+$+H)

EXAMPLE 20

1-{1-[4-(N-acetyl-8-azabicyclo[3.2.1]octanyl-3-oxy)-2-methoxybenzoyl]-piperidin-4-yl}-4H-3,1-benzoxazin-2(1H)-one

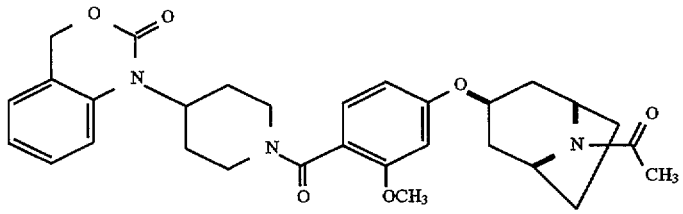

A stirred solution of the compound of EXAMPLE 37 (100 mg, 0.20 mmol) in $CH_2Cl_2$ (2 mL) was cooled to 0° C. Triethylamine (56 mL, 0.40 mmol) and acetic anhydride (30 mL, 0.30 mmol) were added and the solution was allowed to warm to ambient temperature over 14 h. The solvent was removed under reduced pressure to afford a crude oil. The residue was chromatographed on a silica gel column packed in 98:2 $CH_2Cl_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{30}H_{35}N_3O_6 \cdot 1.25\ CH_2Cl_2,\ 0.10\ H_2O)$ C, 58.50; H, 5.92; N, 6.55 Found C, 58.49; H, 5.60; N, 6.48

TLC: $R_f$=0.60 [10% $MeOH(NH_3)$/90% $CH_2Cl_2$]

HPLC (method A): retention time 7.83 min.

FAB MS: m/z 534 ($M^+$+H)

EXAMPLE 21

(±)-1-{1-[4-(1,2,3,4-tetrahydronaphthyl-2-oxy)-2-methoxybenzoyl]-piperidin-4-yl}-4H-3,1-benzoxazin-2(1H)-one

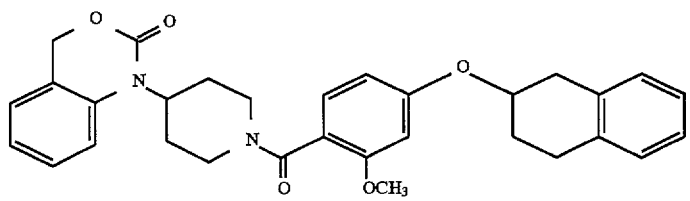

Step 1. A stirred solution of β-tetralone (1 g, 6.84 mmol) in MeOH (34 mL) was cooled to 0° C. under Argon and treated with $NaBH_4$ (258.8 mg, 6.84 mmol). The reaction was stirred over 16 h and allowed to warm to ambient temperature. The solvent was removed under reduced pressure and the crude oil was chromatographed on a silica gel column packed in 95:5 EtOAc:hexanes and eluted with same. The appropriate fractions were combined and the solvent was removed under reduced pressure to give the (1,2,3,4)-tetrahydronaphthalene-2-ol.

Step 2. To a stirred solution of methyl 4-hydroxy-2-methoxybenzoate (435 mg, 2.4 mmol) in dry THF (7 mL) was added triphenylphosphine (945 mg, 3.6 mmol) and the solution was cooled to 0° C. A 2 mL volume of (1,2,3,4)-tetrahydronaphthalene-2-ol (900 mg, 6.08 mmol) and diethyl azodicarboxylate (566 μL, 3.6 mmol) in THF was added dropwise via addition funnel over 0.5 h. The reaction was filtered and the solvent was removed under reduced pressure. The residue was chromatographed on a silica gel column packed in 60:40 hexanes:EtOAc and eluted with same. The appropriate fractions were combined and the solvent removed under reduced pressure to afford methyl 4-[2-(1,2,3,4)-tetrahydronaphthalenoyloxy]-2-methoxybenzoate.

Step 3. To a stirred solution of methyl 4-[2-(1,2,3,4)-tetrahydronaphthalenoyloxy]-2-methoxybenzoate (253 mg, 0.81 mmol) in $THF:H_2O$ (2 mL: 0.5 mL) was added $LiOH \cdot H_2O$ (68 mg, 1.6 mmol). The reaction was heated to 45° C. over 12 h and then cooled to ambient temperature. The solvent was removed under reduced pressure. The crude solid was passed through a plug of silca gel packed in 80:20 hexanes:EtOAc and eluted with same. The solvent was removed under reduced pressure to afford 4-[2-(1,2,3,4)-tetrahydronaphthalenoyloxy]-2-methoxybenzoic acid as a foam.

Step 4. To a stirred solution of 4-[2-(1,2,3,4)-tetrahydronaphthalenoyloxy]-2-methoxybenzoic acid (189 mg, 0.74 mmol) in DMF (5 mL) was added EDC (142.6 mg, 0.74 mmol), HOBT (91.8 mg, 0.74 mmol) and then 1-(4-piperidinyl)-1,2-dihydro-4(H)-3,1-benzoxazin-2-one (172.6 mg, 0.74 mmol). The pH of the solution was adjusted to 8.5 (wetted E. Merck pH sticks) using diisopropylethylamine. The solution was stirred for 12 hours. The solvent was removed under reduced pressure and the residue was partitioned between $CH_2Cl_2$ (10 mL) and 4% aqueous HCl (10 mL). The organic phase was then extracted with water (10 mL), saturated aqueous sodium bicarbonate solution, and brine. The organic phase was dried ($MgSO_4$), filtered and the solvent was removed under reduced pressure. The residue was chromatographed on a silica gel column packed in 98:2 $CH_2Cl_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{31}H_{32}N_2O_5 \cdot 0.70\ H_2O,\ 0.45\ CH_3CN)$ C, 70.47; H, 6.44; N, 6.31 Found C, 70.48; H, 6.27; N, 6.38

TLC: $R_f$=0.75 [10% MeOH(NH$_3$)/90% CH$_2$Cl$_2$]

HPLC (method A): retention time 11.54 min.

FAB MS: m/z 512 (M$^+$+H)

EXAMPLE 22

(±)-1-{1-[4-(1-(methoxycarbonyl)ethoxy)-2-methoxybenzoyl]-piperidin-4-yl}-4H-3,1-benzoxazin-2(1H)-one

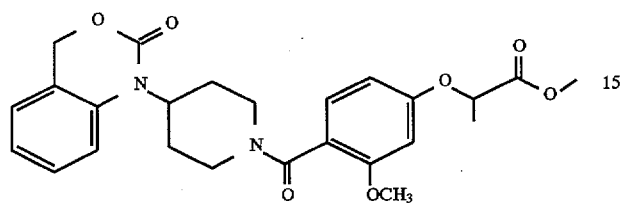

A stirred solution of Compound A (1 g, 2.6 mmol) in DMF (13 mL) was cooled to 0° C. To this was added methyl 2-bromopropionate (564 mg, 3.38 mmol) and cesium carbonate (1.7 g, 5.2 mmol) and the reaction was warmed to ambient temperature over 24 h. The crude solution was filtered through celite and concentrated under reduced pressure. The residue was chromatographed on a silica gel column packed in 95:5 CH$_2$Cl$_2$:MeOH and eluted with same. The appropriate fractions were combined and the solvent was removed under reduced pressure to give an oil which was rechromatographed on a silica gel column packed in 98:2 CH$_2$Cl$_2$:MeOH and eluted with same. The appropriate fractions were combined and the solvent was removed under reduced pressure to afford the title compound. A sample of this material (170 mg) was chromatographed on a preparative HPLC using a gradient of 95:5 to 5:95 water: acetonitrile (0.1%TFA added). The appropriate fractions were combined and freeze dried giving the title compound as a lyophilized solid.

Analysis calculated for (C$_{25}$H$_{28}$N$_2$O$_7$.0.45 CH$_2$Cl$_2$, 0.05 H$_2$O) C, 60.21; H, 5.76; N, 5.52 Found C, 60.26; H, 5.74; N, 5.41

TLC: $R_f$=0.65 110% MeOH(NH$_3$)/90% CH$_2$Cl$_2$]

HPLC (method A): retention time 7.73 min.

FAB MS: m/z 469 (M$^+$+H)

EXAMPLE 23

(±)-1-{1-[4-(1-cyanoethoxy)-2-methoxybenzoyl-piperidin-4-yl}-4H-3,1-benzoxazin-2(1H)-one

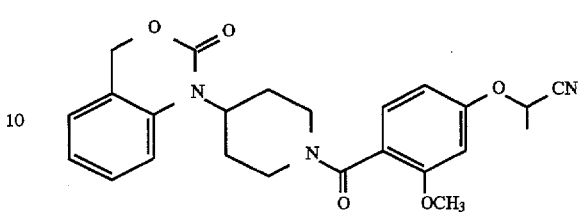

A stirred solution of Compound A (500 mg, 1.3 mmol) in DMF (6.5 mL) was cooled to 0° C. To this was added methyl 2-cyanopropionate (226 mg, 1.69 mmol) and cesium carbonate (845 mg, 2.6 mmol) and the reaction was warmed to ambient temperature over 24 h. The crude solution was filtered through celite and concentrated under reduced pressure. The residue was chromatographed on a silica gel column packed in 98:2 CH$_2$Cl$_2$:MeOH and eluted with same. The appropriate fractions were combined and the solvent was removed under reduced pressure to afford the title compound. A sample of this material (90 mg) was chromatographed on a preparative HPLC using a gradient of 95:5 to 5:95 water: acetonitrile (0.1%TFA added). The appropriate fractions were combined and freeze dried giving the tide compound as a lyophilized solid.

Analysis calculated for (C$_{24}$H$_{25}$N$_3$O$_5$.0.25 CH$_2$Cl$_2$, 0.15 H$_2$O) C, 63.39; H, 5.66; N, 9.15 Found C, 63.37; H, 5.55; N, 9.27

TLC: $R_f$=0.65 110% MeOH(NH$_3$)/90% CH$_2$Cl$_2$]

HPLC (method A): retention time 7.79 min.

FAB MS: m/z 436 (M$^+$+H)

EXAMPLE 24

(±)-1-{1-[4-(1-{2-naphthyl}ethoxy)-2-methoxybenzoyl]-piperidin-4-yl}-4H-3,1-benzoxazin-2(1H)-one

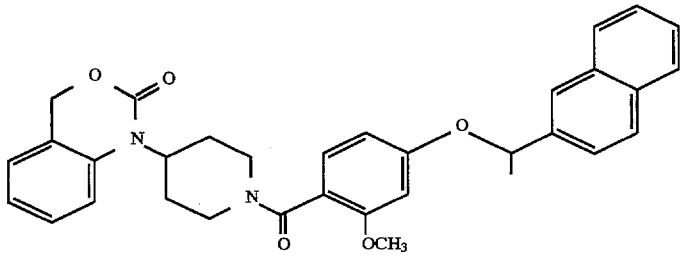

To a stirred solution of Compound A (200 mg, 0.52 mmol) in dry THF (10 mL) was added triphenylphosphine (275 mg, 1.04 mmol) and the solution was cooled to 0° C. A 5 mL volume of α-methyl-2-naphthylmethanol (180 mg, 1.04 mmol) and diethyl azodicarboxylate (165 µL, 1.04 mmol) in THF was added dropwise via syringe over 2 hours. The reaction was filtered and the solvent was removed under reduced pressure and the residue was chromatographed on a silica gel column packed in 60:40 CH$_2$Cl$_2$:EtOAc and eluted with same. The appropriate fractions were combined and the solvent was removed under reduced pressure to give an oil which was rechromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{33}$H$_{32}$N$_2$O$_5$·0.35 H$_2$O) C, 72.99; H, 6.07; N, 5.16 Found C, 72.95; H, 5.96; N, 5.22

TLC: R$_f$=0.35 in 50% EtOAc/50% Hexanes

HPLC (method A): retention time 12.07 min.

FAB MS: m/z 537 (M$^+$+H)

EXAMPLE 25

(±)-1-{1-[4-(1-{2-trifluoromethylphenyl}ethoxy)-2-methoxybenzoyl]-piperidin-4-yl}-4H-3,1-benzoxazin-2(1H)-one

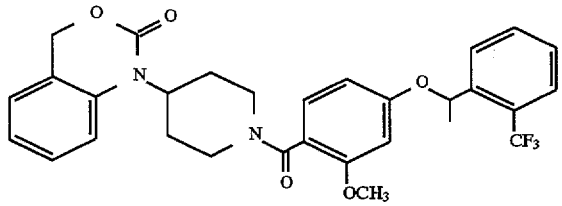

A stirred solution of Compound A (100 mg, 0.26 mmol) in DMF (1.3 mL) was cooled to 0° C. To this was added α-methyl-o-trifluoromethylbenzyl bromide (90.3 mg, 0.34 mmol) and cesium carbonate (171 mg, 0.52 mmol) and the reaction was warmed to ambient temperature over 24 h. The crude solution was filtered through celite and concentrated under reduced pressure. The residue was chromatographed on a preparative HPLC using a gradient of 95:5 to 5:95 water: acetonitrile (0.1%TFA added). The appropriate fractions were combined and freeze dried giving the title compound as a lyophilized solid.

Analysis calculated for (C$_{30}$H$_{29}$N$_2$O$_5$F$_3$·0.55 CH$_2$Cl$_2$) C, 61.02; H.5.05; N, 4.66 Found C, 61.05; H,4.94; N, 4.65

TLC: R$_f$=0.80 [10% MeOH(NH$_3$)/90% CH$_2$Cl$_2$]

HPLC (method A): retention time 10.64 min.

FAB MS: m/z 555 (M$^+$+H)

EXAMPLE 26

1-{1-[4-[N-acetyl-cis-4-aminocyclohexyloxy]-2-methoxybenzoyl]-piperidin-4-yl}-4H-3,1-benzoxazin-2(1H)-one

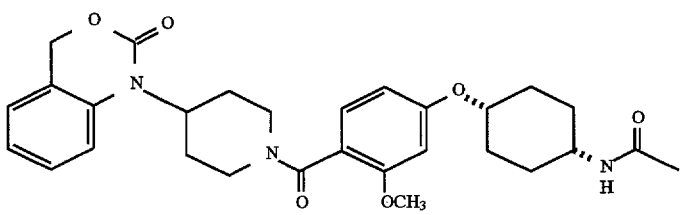

To a stirred solution of the compound of EXAMPLE 16 (52 mg, 0.1 mmol) in CH$_2$Cl$_2$ (1 mL) was added diisopropylethylamine (38.3 μL, 0.22 mmol) and acetic anhydride (12.5 μL, 0.12 mmol). The solution was stirred at ambient temperature for 24 h. The solvent was removed under reduced pressure and the residue was partitioned between CH$_2$Cl$_2$ (5 mL) and 4% aqueous HCl (5 mL). The organic phase was then extracted with water (5 mL), saturated aqueous sodium bicarbonate solution, and brine. The organic phase was dried (MgSO$_4$), filtered and the solvent was removed under reduced pressure. The residue was chromatographed on a silica gel column packed in 90:10 CH$_2$Cl$_2$:MeOH(NH$_3$) and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{29}$H$_{33}$N$_3$O$_6$·0.65 CH$_2$Cl$_2$, 0.80 MeOH) C, 60.91; H, 6.30; N, 7.00 Found C, 60.93; H, 6.31; N, 7.22

TLC: R$_f$=0.80 [20% MeOH(NH$_3$)/80% CH$_2$Cl$_2$]

HPLC (method A): retention time 7.01 min.

FAB MS: m/z 522 (M$^+$+H)

EXAMPLE 27

(±)-1-{1-[4-(1-{tetrazol-5-yl}ethoxy)-2-methoxybenzoyl]1-piperidin-4-yl}-4H-3,1-benzoxazin-2(1H)-one A solution of the compound of EXAMPLE 23 (200 mg, 0.46 mmol) in DMF (500 mL) was heated to 100° C. under N₂ atmosphere. To the stirred solution was added sodium azide (33.2 mg, 0.51 mmol), lithium chloride (20 mg, 0.46 mmol) and ammonium chloride (2 mg, 0.05 mmol). The solution was heated over 16 h and then more sodium azide (33.2 mg, 0.51 mmol), lithium chloride (20 mg, 0.46 mmol) and ammonium chloride (2 mg, 0.05 mmol) were added. The solution was heated for another 16 hours and then cooled to ambient temperature. The solvent was removed under reduced pressure and the crude residue dissolved in H₂O (10 mL). The aqueous solution was made basic with 10% NaOH (1 mL) and stripped to dryness. The crude residue was taken up in 5% HCl (2 mL) and again stripped to dryness. The crude tetrazole was then taken up in CH₂Cl₂ (10 mL) and washed with H₂O (5 mL). The organic phase was dried (MgSO₄) and filtered. The solvent was removed under reduced pressure to afford a crude foam. The product was chromatographed on a silica gel column packed in 100% CH₂Cl₂ and eluted with a gradient solvent system to 70% CH₂Cl₂:30% MeOH(NH₃). The appropriate fractions were combined and the solvent was removed under reduced pressure to give an oil which was dissolved in 9:1 acetonitrile:water and freeze dried giving the title compound as a lyophilized solid.

Analysis calculated for (C$_{24}$H$_{26}$N$_6$O$_5$·0.60 CH$_2$Cl$_2$, 1.75 MeOH) C, 54.05; H, 5.89; N, 14.35 Found C, 54.06; H, 5.58; N, 14.15

TLC: R$_f$=0.10 in 10% MeOH(NH$_3$)/90% CH$_2$Cl$_2$]

HPLC (method A): retention time 6.69 min.

FAB MS: m/z 479 (M⁺+H)

EXAMPLE 28

(±)-1-{1-[4-(1-{pyrazin-2-yl}ethoxy)-2-methoxybenzoyl]-piperidin-4-yl}-4H-3,1-benzoxazin-2(1H)-one

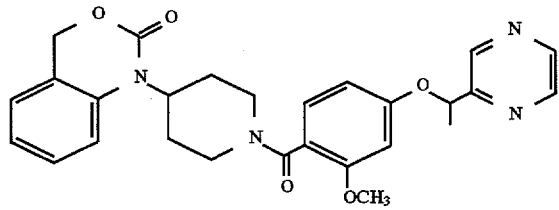

Step 1. To a stirred solution of acetylpyrazine (2 g, 16 mmol) in 1:1 THF:MeOH was added sodium borohydride (620 mg, 16 mmol) and stirred overnight. The mixture was filtered and the solvent removed under reduced pressure. The residue was dissolved in 95:5 CH₂Cl₂:MeOH and passed through a plug of silica in a Buchner funnel and eluted with same. The solvent was removed from the eluent under reduced pressure and the resulting oil which was obtained was determined by NMR to be clean α-methyl-2-pyrazinylmethanol.

Step 2. To a stirred solution of Compound A (200 mg, 0.52 mmol) in dry THF (10 mL) was added triphenylphosphine (275 mg, 1.04 mmol) and the solution was cooled to 0° C. A 5 mL volume of the previously prepared α-methyl-2-pyrazinylmethanol (130 mg, 1.04 mmol) and diethyl azodicarboxylate (165 µL, 1.04 mmol) in THF was added dropwise via syringe over 2 hours. The reaction was filtered and the solvent was removed under reduced pressure and the residue was chromatographed on a silica gel column packed in 60:40 CH₂Cl₂:EtOAc and eluted with same. The appropriate fractions were combined and the solvent was removed under reduced pressure to give an oil which was rechromatographed on a silica gel column packed in 98:2 CH₂Cl₂:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{27}$H$_{28}$N$_4$O$_5$·0.70 H$_2$O) C, 64.70; H, 5.91; N, 11.18 Found C, 64.66; H, 5.68; N, 11.23

TLC: R$_f$=0.4 in 5% MeOH/95% CH$_2$Cl$_2$

HPLC (method A): retention time 8.63 min.

FAB MS: m/z 489 (M⁺+H)

EXAMPLE 29

1-{1-[4-(4-oxocyclohexyloxy)-2-methoxybenzoyl]-piperidin-4-yl}-4H-3,1-benzoxazin-2(1H)-one

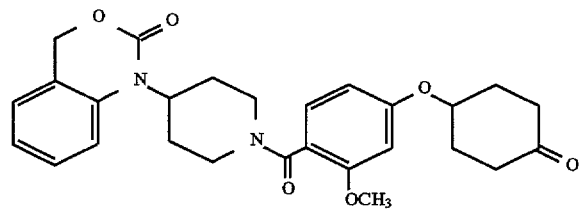

Step 1. To a stirred solution of methyl 4-hydroxy-2-methoxybenzoate (865 mg, 4.75 mmol) in dry THF (6 mL) was added triphenylphosphine (1.25 g, 4.75 mmol) and the solution was cooled to 0° C. A 7.0 mL volume of 1,4-dioxaspiro[4.5]-decan-8-ol (0.5 g, 3.65 mmol) and diethyl azodicarboxylate (748 mL, 4.75 mmol) in THF was added dropwise via addition funnel over 0.5 h. The reaction was filtered and the solvent was removed under reduced pressure. The residue was chromatographed on a silica gel column packed in 70:30 hexanes:EtOAc and eluted with same. The appropriate fractions were combined and the solvent removed under reduced pressure to afford methyl 4-[8-(1,4-dioxaspiro[4.5]-decanoyloxy]-2-methoxybenzoate.

Step 2. To a stirred solution of methyl 4-[8-(1,4-dioxaspiro[4,5-decanoyloxy]-2-methoxybenzoate (430 mg, 1.34 mmol) in THF:H₂O (12.5 mL: 2.5 mL) was added LiOH.H₂O (170.8 mg, 4.0 mmol). The reaction was heated to 45° C. over 12 h and then cooled to ambient temperature. The solvent was removed under reduced pressure. The crude solid was passed through a plug of silca gel packed in 50:50 MeOH:CH₂Cl₂ and eluted with same. The solvent was removed under reduced pressure to afford 4-[8-(1,4-dioxaspiro[4.5]-decanoyloxy)]-2-methoxybenzoic acid as a white solid.

Step 3. To a stirred solution of 4-[8-(1,4-dioxaspiro[4.5] -decanoyloxy)]-2-methoxybenzoic acid (390 mg, 1.27 mmol) in DMF (2 mL) was added EDC (291.4 mg, 1.52 mmol), HOBT (232.6 mg, 1.52 mmol) and then 1-(4-piperidinyl)-1,2-dihydro-4(H)-3,1-benzoxazin-2-one (353 mg, 1.52 mmol). The pH of the solution was adjusted to 8.5 (wetted E. Merck pH sticks) using diisopropylethylamine. The solution was stirred for 16 hours. The solvent was removed under reduced pressure and the residue was partitioned between CH₂Cl₂ (10 mL) and 4% aqueous HCl (5 mL). The organic phase was then extracted with water (5 mL), saturated aqueous sodium bicarbonate solution, and brine. The organic phase was dried (MgSO₄), filtered and the solvent was removed under reduced pressure. The residue was chromatographed on a silica gel column packed in 98:2 CH₂Cl₂:MeOH and eluted with same. The appropriate fractions were combined and the solvent was removed under reduced pressure to give 1-{1-[4-(1,4-dioxaspiro-[4.5]-decanoyl-8-oxy)-2-methoxybenzoyl]-piperidin-4-yl}-4H-3,1-benzoxazin-2(1H)-one.

Step 4. To a stirred solution of 1-{1-[4-(1,4-dioxaspiro[4.5]-decanoyl-8-oxy)-2-methoxybenzoyl]-piperidin-4-yl}-4H-3,1-benzoxazin-2(1H)-one (90 mg, 0.17 mmol) in wet acetone (2 mL) at ambient temperature was added HOAc (~250 μL). The solution was allowed to stir at ambient temperature for one week and then the solvent was removed under reduced pressure. The crude product was dissolved in CH₂Cl₂ (10 mL) and extracted with H₂O (2×5 mL). The organic phase was dried (MgSO₄), filtered and the solvent removed under reduced pressure. The white foam was dissolved in 9:1 acetonitrile: water and freeze dried giving the title compound as a lyophilized solid.

Analysis calculated for (C₂₇H₃₀N₂O₆·0.2 CH₂Cl₂, 0.80 MeOH) C, 64.52; H, 6.48; N, 5.39 Found C, 64.52; H, 6.48; N, 5.39

TLC: R_f=0.60 [20% MeOH(NH₃)/80% CH₂Cl₂]

HPLC (method A): retention time 7.56 min.

FAB MS: m/z 521 (M⁺+H)

EXAMPLE 30

(±)-1-{1-[4-(1-{piperidin-4-yl}ethoxy)-2-methoxybenzoyl]-piperidin-4-yl}-4H-3,1-benzoxazin-2(1H)-one

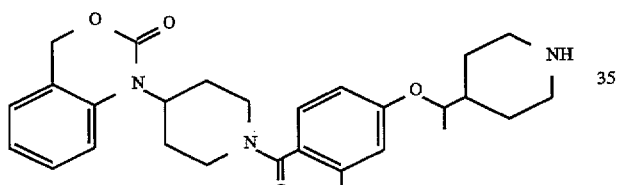

Step 1. To α-methylpiperidinylmethanol (2.45 g, 19 mmol) in CH₂Cl₂ (25 mL) was added diisopropylethylamine (3.20 mL, 19 mmol) followed by di-tert-butyl dicarbonate (4.14 g, 19 mmol) and the reaction was stirred for 2 hours. The reaction was extracted with 10% citric acid (25 mL) followed by saturated aqueous sodium bicarbonate (25 mL), water, and brine and dried with sodium sulfate and filtered. The solvent was removed under reduced pressure. The residue was chromatographed on a silica gel column packed in 30:70 EtOAc:hexanes and eluted with same. The appropriate fractions were combined and the solvent was removed under reduced pressure to give N-BOC-α-methylpiperidinylmethanol.

Step 2. To a stirred solution of Compound A (200 mg, 0.52 mmol) in dry THF (10 mL) was added triphenylphosphine (275 mg, 1.04 mmol) and the solution was cooled to 0° C. A 5 mL volume of the previously prepared N-BOC-α-methylpiperidinylmethanol (240 mg, 1.04 mmol) and diethyl azodicarboxylate (165 μL, 1.04 mmol) in THF was added dropwise via syringe over 2 hours. The reaction was filtered and the solvent was removed under reduced pressure and the residue was chromatographed on a silica gel column packed in 60:40 CH₂Cl₂:EtOAc and eluted with same. The appropriate fractions were combined and the solvent was removed under reduced pressure to give an oil which was a mixture of the desired product and triphenylphosphine oxide. This mixture was treated with 25% TFA in CH₂Cl₂ (50 mL) and stirred at room temperature for 1 hour. The solvent was removed under reduced pressure and the residue was partitioned between CH₂Cl₂ and 4% aqueous HCL (50mL:50mL). The aqueous layer was extracted twice with CH₂Cl₂ then made basic with the addition of solid sodium bicarbonate. The basic solution was extracted 3 times with CH₂Cl₂. The combined organic phase was extracted with water (50 mL) and brine (50 mL) and dried with MgSO₄. The organic phase was filtered and concentrated under reduced pressure. The residue was chromatographed on a preparative HPLC using a gradient of 95:5 to 5:95 water: acetonitrile (0.1%TFA added). The appropriate fractions were combined and freeze dried giving the title compound as a lyophilized solid.

Analysis calculated for (C₂₆H₃₀N₂O₆·0.50 TFA, 0.50 H₂O) C, 62.23; H, 6.51; N, 7.51 Found C, 62.26; H, 6.51; N, 7.57

TLC: R_f=0.4 in 5% MeOH/95% CH₂Cl₂

HPLC (method A): retention time 7.41 min.

FAB MS: m/z 494 (M⁺+H)

EXAMPLE 31

(±)-1-{1-[4-(1-{N-Acetylpiperidin-4-yl}ethoxy)-2-methoxybenzoyl]-piperidin-4-yl}-4H-3,1-benzoxazin-2(1H)-one

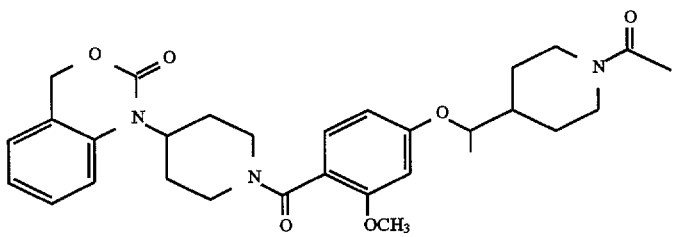

To a stirred solution of the product of EXAMPLE 30 (50 mg, 0.09 mmol) in CH₂Cl₂ (10 mL) was added acetic anhydride (12 μL, 0.135 mmol) followed by diisopropylethylamine (12 μL, 0.135 mmol) and the solution was stirred at room temperature for 1 h. The solvent was removed under reduced pressure and the residue was partitioned between CH₂Cl₂ (10 mL) and 4% aqueous HCL (10 mL). The organic layer was washed with saturated aqueous sodium bicarbonate (10 mL), water (10 mL), and brine (10 mL) and dried with MgSO₄ and filtered. The solvent was removed under reduced pressure to give a foam which was dissolved in 9:1 acetonitrile:water and freeze dried giving the title compound as a lyophilized solid.

Analysis calculated for $(C_{26}H_{30}N_2O_6 \cdot 1.45\ H_2O)$ C, 64.13; H, 7.16; N, 7.48 Found C, 64.16; H, 6.82; N, 7.53

TLC: $R_f=0.4$ in 5% MeOH/95% $CH_2Cl_2$

HPLC (method A): retention time 7.83 min.

FAB MS: m/z 536 (M$^+$+H)

EXAMPLE 32

(±)-1-{1-[4-(1-{thiazol-2-yl}ethoxy)-2-methoxybenzoyl]-piperidin-4-yl}-4H-3,1-benzoxazin-2(1H)-one

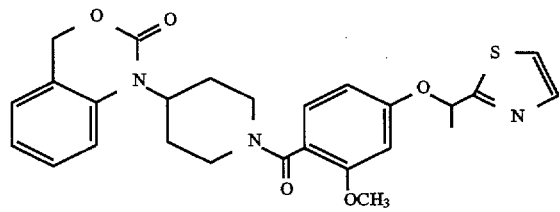

Step 1. To a stirred solution of 2-acetylthiazole (2 g, 16 mmol) in 1:1 THF:MeOH was added sodium borohydride (620 mg, 16 mmol) and stirred overnight. The reaction was filtered and the solvent removed under reduced pressure. The residue was dissolved in 95:5 $CH_2Cl_2$:MeOH and passed through a plug of silica in a Buchner funnel and eluted with same. The solvent was removed under reduced pressure to give α-methyl-2-thiazolylmethanol.

Step 2. To a stirred solution of Compound A (200 mg, 0.52 mmol) in dry THF (10 mL) was added triphenylphosphine (275 mg, 1.04 mmol) and the solution was cooled to 0° C. A 5 mL volume of the previously prepared α-methyl-2-thiazolylmethanol (130 mg, 1.04 mmol) and diethyl azodicarboxylate (165 μL, 1.04 mmol) in THF was added dropwise via syringe over 2 hours. The reaction was filtered and the solvent was removed under reduced pressure and the residue was chromatographed on a silica gel column packed in 60:40 $CH_2Cl_2$:EtOAc EtOAc and eluted with same. The appropriate fractions were combined and the solvent was removed under reduced pressure to give an oil which was rechromatographed on a silica gel column packed in 98:2 $CH_2Cl_2$:MeOH and eluted with same. The appropriate fractions were combined and the solvent was removed under reduced pressure. The residue was chromatographed on a preparative HPLC using a gradient of 95:5 to 5:95 water:acetonitrile (0.1% TFA added). The appropriate fractions were combined and freeze dried giving the title compound as a lyophilized solid.

Analysis calculated for $(C_{26}H_{27}N_3O_5S \cdot 0.75\ TFA,\ 0.1\ H_2O)$ C, 56.85; H, 4.85; N, 7.23 Found C, 56.84; H, 4.86; N, 6.94

TLC: $R_f=0.5$ in 5% MeOH/95% $CH_2Cl_2$

HPLC (method A): retention time 9.4 min.

FAB MS: m/z 536 (M$^+$+H)

EXAMPLE 33

(±)-1-{1-[4-(1-{imidazol-4(5)-yl}ethoxy)-2-methoxybenzoyl]-piperidin-4-yl}-4H-3,1-benzoxazin-2(1H)-one

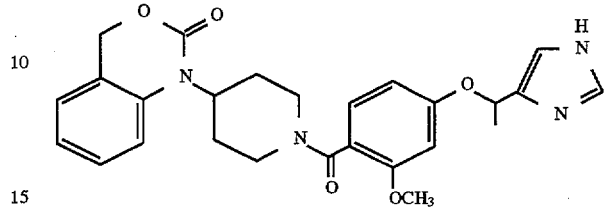

To a stirred solution of Compound A (200 mg, 0.52 mmol) in dry THF (10 mL) was added triphenylphosphine (275 mg, 1.04 mmol) and the solution was cooled to 0° C. A 5 mL volume of N-trityl-1-(imidazol-4(5)yl)ethanol (125 mg, 1.04 mmol, prepared according to the procedure disclosed in R. M. Turner et al., *J. Org. Chem.*, 1991, 57, 5739) and diethyl azodicarboxylate (165 μL, 1.04 mmol) in THF was added dropwise via syringe over 2 hours. The reaction was filtered and the solvent was removed under reduced pressure. The residue was chromatographed on a silica gel column packed in 60:40 $CH_2Cl_2$:EtOAc and eluted with same. The appropriate fractions were combined and the solvent was removed under reduced pressure to give an oil which was rechromatographed on a silica gel column packed in 98:2 $CH_2Cl_2$:MeOH and eluted with same. The appropriate fractions were combined and the solvent was removed under reduced pressure. The residue was chromatographed on a preparative HPLC using a gradient of 95:5 to 5:95 water:acetonitrile (0.1% TFA added). The appropriate fractions were combined and the solvent removed under reduced pressure to afford 1-{1-[4-(1-{imidazol-4(5)-yl}-2-methoxybenzoyl]-piperidin-4-yl}-4H-3,1-benzoxazin-2(1H)-one as a white foam.

Step 2: To a stirred solution of 1-{1-[4-(1-{imidazol-4(5)-yl}-2-methoxybenzoyl]-piperidin-4-yl}-4H-3,1-benzoxazin-2(1H)-one (250 mg, 0.44 mg) in $CH_2Cl_2$ (20 mL) was added trifluoroacetic acid (5 mL). The solution was stirred at ambient temperature for 1 h and then the solvent was removed under reduced pressure. The crude product was chromatographed on a silica gel column packed with 98:2 $CH_2Cl_2$:MeOH and eluted with same. The appropriate fractions were combined and the solvent removed under reduced pressure. The product was dissolved in 95:5 acetonitrile:$H_2O$ and freeze dried to give the title compound as a white lyophilized solid.

Analysis calculated for $(C_{26}H_{28}N_4O_5 \cdot 2.15\ TFA,\ 1.45\ H_2O)$ C, 48.66; H, 4.45; N, 7.49 Found C, 48.67; H, 4.25; N, 7.88

TLC: $R_f=0.3$ in 4.5% MeOH/95% $CH_2Cl_2$/0.5% $NH_4OH$

HPLC (method A): retention time 8.02 min.

FAB MS: m/z 477 (M$^+$+H)

EXAMPLE 34

(±)-1-{1-[4-(1-hydroxy-2-propyloxy)-2-methoxybenzoyl]-piperidin-4-yl}-4H-3,1-benzoxazin-2(1H)-one

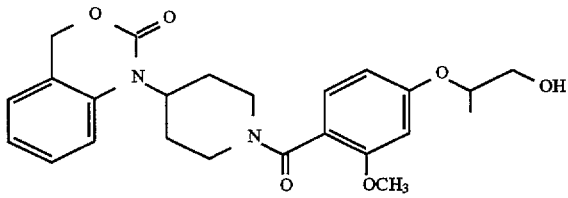

A stirred solution of the compound of EXAMPLE 22 (1 g, 2.1 mmol) in THF (10.5 mL) was cooled to 0° C. with stirring. To the solution was added LiBH₄ (46.5 mg, 2.1 mmol) and the solution was allowed to warm to ambient temperature over 16 h. To the stirred solution was added another equivalent of LiBH₄ (46.5 mg, 2.1 mmol) and the solution was allowed to stir over another 16 h. The solvent was then removed under reduced pressure. The crude residue was chromatographed on a silica gel column packed in 96:4 CH₂Cl₂:MeOH (NH₃) and eluted with same. The appropriate fractions were combined and the solvent was removed under reduced pressure to give a foam which was dissolved in 9:1 acetonitrile:water and freeze dried giving the title compound as a lyophilized solid.

Analysis calculated for (C₂₄H₂₈N₂O₆.0.60 CH₂Cl₂, 0.05 H₂O) C, 60.01; H, 6.00 N, 5.69 Found C, 59.99; H, 5.87; N, 5.80

TLC: R$_f$=0.70 [10% MeOH(NH₃)/90% CH₂Cl₂]

HPLC (method A): retention time 6.69 min.

FAB MS: m/z 441 (M⁺+H)

EXAMPLE 35

(±)-1-{1-[4-(1-{4-morpholino}-2-propyloxy)-2-methoxybenzoyl]-piperidin-4-yl}-4H-3,1-benzoxazin-2(1H)-one

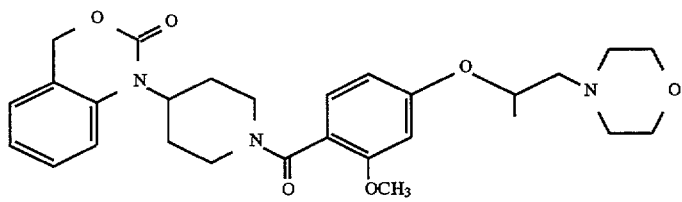

Step 1. A stirred solution of oxalyl chloride (134 μL, 1.54 mmol) in CH₂Cl₂ (28 mL) was cooled to −78° C. To this was added dropwise DMSO (218 μL, 3.08 mmol) and then the compound of EXAMPLE 34 (600 mg, 1.40 mmol) dissolved in CH₂Cl₂ (5 mL). The solution was stirred 15 minutes and then triethylamine (7 mmol, 983 μL) was added and the reaction stirred an additional 15 minutes. The reaction was allowed to warm to ambient temperature over 1 h. The reaction was quenched with H₂O (30 mL) and extracted with CH₂Cl₂ (2×20 mL). The organic phase was washed with sat. NaCl (20 mL), dried (MgSO₄) and filtered. The solvent was removed under reduced pressure to afford the aldehyde as a white foam which was used without further purification.

Step 2. The crude (±)-1-{1-[4-(1-carboxaldehyde-2-propyloxy)-2-methoxybenzoyl]-piperidin-4-yl}-4H-3,1-benzoxazin-2(1H)-one (100 mg, 0.23 mmol) was dissolved in MeOH and cooled to 0° C. To the stirred solution was added morpholine (25 μL, 0.28 mmol), NaCNBH₃ (27 mg, 0.46 mmol) and HOAc (2 drops). The solution was warmed to ambient temperature over 16 h and then the solvent removed under reduced pressure to afford a crude solid. The product was chromatographed on a silica gel column packed in 96:4 CH₂Cl₂:MeOH(NH₃) and eluted with same. The appropriate fractions were combined and the solvent removed under reduced pressure to afford an impure quantity of the desired product. The residue was rechromatographed on a preparative HPLC using a gradient of 95:5 to 5:95 water:acetonitrile (0.1% TFA added). The appropriate fractions were combined and freeze dried giving the title compound as a lyophilized solid.

Analysis calculated for (C₂₈H₃₅N₃O₆.0.05 CH₂Cl₂, 1.80 TFA) C, 52.86; H, 5.17; N, 5.84 Found C, 52.82; H, 5.17; N, 5.94

TLC: R$_f$=0.85 [10% MeOH(NH₃)/90% CH₂Cl₂]

HPLC (method A): retention time 5.96 min.

FAB MS: m/z 510 (M⁺+H)

EXAMPLE 36

(±)-1-{1-[4-(1-{N,N-diethylamino}-2-propyloxy)-2-methoxybenzoyl]-piperidin-4-yl}-4H-3,1-benzoxazin-2(1H)-one

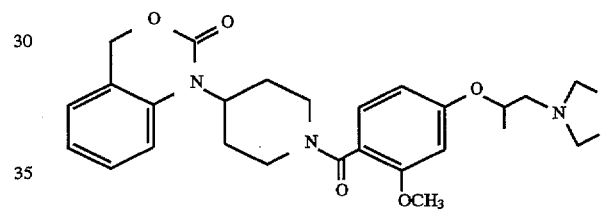

A stirred solution of the crude (±)-1-{1-[4-(1-carboxaldehyde-2-propyloxy)-2-methoxybenzoyl]-piperidin-4-yl}-4H-3,1-benzoxazin-2(1H)-one (100 mg, 0.23 mmol) from the previous Example in MeOH (1.15 mL) was cooled to 0° C. To the stirred solution was added N,N-diethylamine (30 μL, 0.46 mmol), NaCNBH₃ (27 mg, 0.46 mmol) and HOAc (2 drops). The solution was warmed to ambient temperature over 16 h and then the solvent removed under reduced pressure to afford a crude solid. The crude product was taken up in CH₂Cl₂ (10 mL) and extracted with H₂O (2×10 mL). The organic phase was washed with sat. NaCl (20 mL), dried (MgSO₄) and filtered. The solvent was removed under reduced pressure to afford a crude foam. The foam was chromatographed on a silica gel column packed in 96:4 CH₂Cl₂:MeOH(NH₃) and eluted with same. The appropriate fractions were combined and the solvent was removed under reduced pressure to give a foam which was dissolved in 9:1 acetonitrile:water and freeze dried giving the title compound as a lyophilized solid.

Analysis calculated for ($C_{28}H_{37}N_3O_5 \cdot 1.20\ CH_2Cl_2$, 0.35 $CH_3CN$) C, 58.68; H, 6.66; N, 7.67 Found C, 58.57; H, 6.73; N, 7.67

TLC: $R_f$=0.50 [10% MeOH($NH_3$)/90% $CH_2Cl_2$]

HPLC (method A): retention time 6.26 min.

FAB MS: m/z 496 ($M^+$+H)

EXAMPLE 37

1-{1-[4-(8-azabicyclo[3.2.1]octanyl-3-oxy)-2-methoxybenzoyl]-piperidin-4-yl}-4H-3,1-benzoxazin-2(1H)-one

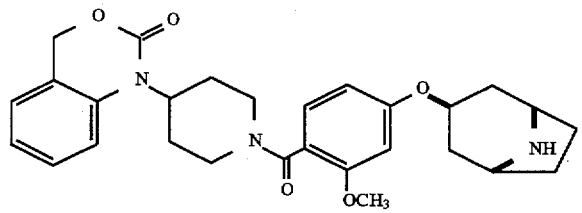

Step 1. To a stirred solution of N-methyltropinol (5 g, 35 mmol) was added triethylamine (7.15 mL, 52.5 mmol), acetic anhydride (3.9 mL, 42.5 mmol) and catalytic N,N-dimethylaminopyridine (ca. 50 mg). The solution was stirred at ambient temperature for 48 h. The solvent was removed under reduced pressure and the crude residue dissolved in $H_2O$ (50 mL). The aqueous solution was made basic with 10% NaOH (20 mL) and extracted with $CH_2Cl_2$ (3×50 mL). The organic phase was dried ($MgSO_4$), filtered and the solvent removed under reduced pressure. The crude product was chromatographed on a silica gel column packed in 9:1 hexanes:EtOAc and eluted with same. The appropriate fractions were combined and the solvent was removed under reduced pressure to give the N-methyltropane acetate as a white solid.

Step 2. A stirred solution of N-methyltropane acetate (4.24 g, 23.2 mmol) in dichloroethane (23 mL) was cooled to 0° C. and α-chloroethylchloroformate (5.0 mL, 46.4 mmol) was added. The solution was heated to reflux for 1 h and cooled to ambient temperature. The solvent was removed under reduced pressure and the residue redissolved in MeOH (20 mL). This solution was heated to reflux with stirring over 16 h. The solution was cooled to ambient temperature and the solvent again removed under reduced pressure. The crude sample was chromatographed on a silica gel column packed in 9:1 hexanes:EtOAc and eluted with same. The appropriate fractions were combined and the solvent was removed under reduced pressure to give the O-acetyltropine.

Step 3. To a stirred solution of O-acetyltropine (3.20 g, 18.9 mmol) in $CH_2Cl_2$ (94.5 mL) was added diisopropylethylamine (6.60 mL, 37.9 mmol) and then di-t-butyldicarbonate (4.13 g, 18.9 mmol). The solution was stirred at ambient temperature over 15 h. The reaction solution was diluted with 5% HCl (50 mL) and extracted with $CH_2Cl_2$ (2×50 mL). The organic phases were combined, dried ($MgSO_4$), filtered and the solvent removed under reduced pressure to afford the N-Boc-O-acetyltropine as a clear oil that solidified overnight.

Step 4. To a stirred solution of N-Boc-O-acetyltropine (2.17 g, 8.1 mmol) in THF:$H_2O$ (20 mL:2 mL) was added LiOH.$H_2O$ (1.1 g, 32.3 mmol). The solution was stirred over 24 h and then made acidic with 5% HCl (pH N~5). The solution was extracted with $CH_2Cl_2$ (2×20 mL). The organic phases were combined, dried ($MgSO_4$), and filtered. The solvent was removed under reduced pressure to afford the N-Boc-tropinol as a white solid.

Step 5. To a stirred solution of Compound A (300 mg, 0.79 mmol) in dry THF (2 mL) was added triphenylphosphine (310 mg, 1.18 mmol) and the solution was cooled to 0° C. A 2 mL volume of the previously prepared N-Boc-tropinol (267 mg, 1.18 mmol) and diethyl azodicarboxylate (185 μL, 1.18 mmol) in THF was added dropwise via syringe over 2 hours. The reaction was filtered and the solvent was removed under reduced pressure. The residue was chromatographed on a silica gel column packed in 95:5 $CH_2Cl_2$:MeOH($NH_3$) and eluted with same. The appropriate fractions were combined and the solvent was removed under reduced pressure to give 1-{1-[4-(4-N-tert-butylcarbonyloxytropanoyloxy)-2-methoxybenzoyl]-piperidin-4-yl}-4H-3,1-benzoxazin-2(1H)-one.

Step 6. A stirred solution of 1-{1-[4-(4-N-tert-butylcarbonyloxytropanoyloxy)-2-methoxybenzoyl]-piperidin-4-yl}-4H-3,1-benzoxazin-2(1H)-one (400 mg, 0.68 mmol) in MeOH (5 mL) was cooled to 0° C. and anhydrous HCl was bubbled in for 5 minutes. The reaction solution was allowed to stir 1 h and then the solvent was removed under reduced pressure. The residue was chromatographed on a silica gel column packed in 90:10 $CH_2Cl_2$:MeOH($NH_3$) and eluted with same. The appropriate fractions were combined and the solvent was removed under reduced pressure to afford a white foam. The solid was dissolved in 95:5 $H_2O$:acetonitrile and freeze dried giving the title compound as a lyophilized solid.

Analysis calculated for ($C_{28}H_{33}N_3O_5 \cdot 2.45$ HCl) C, 57.89; H, 6.15; N, 7.73 Found C, 57.64; H, 6.25; N, 7.73

TLC: $R_f$=0.20 [10% MeOH($NH_3$)/90% $CH_2Cl_2$]

HPLC (method A): retention time 5.99 min.

FAB MS: m/z 492 ($M^+$+H)

EXAMPLE 38

(±)-1-{1-[4-(1-fluoro-2-propyloxy)-2-methoxybenzoyl]-piperidin-4-yl}-4H-3,1-benzoxazin-2(1H)-one

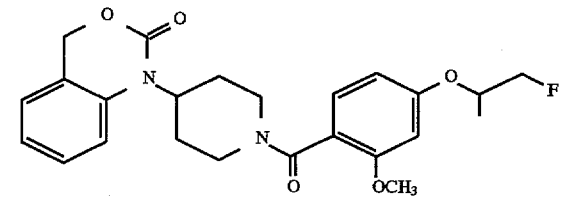

To a stirred solution of the compound of EXAMPLE 34 (100 mg, 0.23 mmol) in $CH_2Cl_2$ (4 mL) was added pyridine (36.5 μL, 0.46 mmol) and then diethylaminosulfur trifluoride (40.16 μL, 0.30 mmol). The solution was stirred at ambient temperature for 16 h. The reaction solution was then diluted with $H_2O$ (5 mL) and extracted with $CH_2Cl_2$ (5 mL). The organic phase was dried ($MgSO_4$) and filtered. The solvent was removed under reduced pressure to afford a white foam. The crude solid was chromatographed on a silica gel column packed in 98% $CH_2Cl_2$:2% MeOH($NH_3$) and eluted with same. The appropriate fractions were combined and the solvent was removed under reduced pressure to afford a white foam. The solid was dissolved in 95:5 $H_2O$:acetonitrile and freeze dried giving the title compound as a lyophilized solid.

Analysis calculated for ($C_{24}H_{27}N_2O_5F$. 0.2 $CH_2Cl_2$) C, 63.25; H, 6.01; N, 6.10 Found C, 63.29; H, 5.98; N, 6.16

TLC: $R_f$=0.85 120% MeOH($NH_3$)/80% $CH_2Cl_2$]

HPLC (method A): retention time 8.10 min.

FAB MS: m/z 443 ($M^+$+H)

EXAMPLE 39

(±)-1-{1-[4-(3-hydroxy-2-butyloxy)-2-methoxybenzoyl]-piperidin-4-yl}-4H-3,1-benzoxazin-2(1H)-one

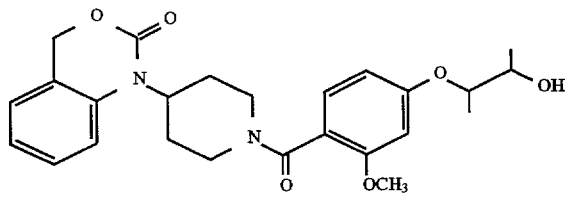

A stirred solution of (±)-1-{1-[4-(1-carboxaldehyde-2-propyloxy)-2-methoxybenzoyl]-piperidin-4-yl}-4H-3,1-benzoxazin-2(1H)-one (100 mg, 0.23 mmol) from Example 35 in THF (1.15 mL) was cooled to −78° C. and treated with MeMgBr (83 μL, 0.25 mmol). The solution was allowed to warm to ambient temperature over 14 h and then quenched with $H_2O$ (10 mL). Then reaction was extracted with $CH_2Cl_2$ (2×10 mL), the organic layers combined, dried ($MgSO_4$) and filtered. The solvent was removed under reduced pressure to afford a crude foam. The solid was chromatographed on a preparative HPLC using a gradient of 95:5 to 5:95 water:acetonitrile (0.1% TFA added). The appropriate fractions were combined and freeze dried giving the title compound as a lyophilized solid.

Analysis calculated for ($C_{25}H_{30}N_2O_6$.0.85 $CH_2Cl_2$, 0.10 $H_2O$) C, 58.74; H, 6.08; N, 5.30 Found C, 58.69; H, 5.79; N, 5.39

TLC: $R_f$=0.80 [10% MeOH($NH_3$)/90% $CH_2Cl_2$]

HPLC (method A): retention time 6.92 min.

FAB MS: m/z 455 ($M^+$+H)

EXAMPLE 40

(±)-1-{1-[4-(1-methoxy-2-propyloxy)-2-methoxybenzoyl]-piperidin-4-yl}-4H-3,1-benzoxazin-2(1H)-one

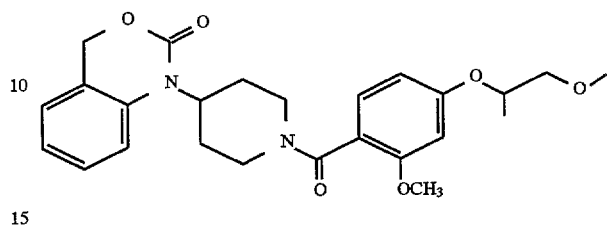

To a stirred solution of the compound of EXAMPLE 34 (100 mg, 0.23 mmol) in THF (1.15 mL) was added potassium tert-butoxide (230 μL, 1.0M, 0.23 mmol) and then methyl iodide (71.5 μL, 1.15 mmol). The reaction was stirred 3 h and then additional potassium tert-butoxide (115 μL, 0.11 mmol) was added. The reaction was stirred an additional 1 h and then the solvent was removed under reduced pressure. The crude solid was chromatographed on a silica gel column packed in 100% $CH_2Cl_2$ and eluted with same. The solid was rechromatographed on a preparative HPLC using a gradient of 95:5 to 5:95 water:acetonitrile (0.1% TFA added). The appropriate fractions were combined and freeze dried giving the title compound as a lyophilized solid.

Analysis calculated for ($C_{25}H_{30}N_2O_6$.0.90 $CH_2Cl_2$) C, 58.58; H, 6.04; N, 5.28 Found C, 58.61; H, 5.94; N, 5.39

TLC: $R_f$=0.80 [10% MeOH($NH_3$)/90% $CH_2Cl_2$]

HPLC (method A): retention time 7.85 min.

FAB MS: m/z 455 ($M^+$+H)

EXAMPLE 41

1-{1-[4-(4-{8-[N-oxo-2-methyl-3-pyridylmethyl]-8-azabicyclo[3.2.1]octanyl-3-oxy}-2-methoxybenzoyl]-piperidin-4-yl}-4H-3,1-benzoxazin-2(1H)-one

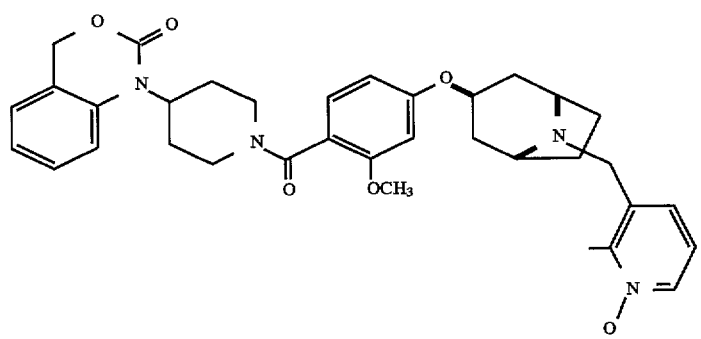

A stirred solution of the compound of EXAMPLE 37 (100 mg, 0.20 mmol) in $CH_2Cl_2$ (2 mL) was cooled to 0° C. Diisopropylethylamine (104.7 μL, 0.60 mmol) and 2-methyl-3-chloromethylpyridine-N-oxide (47.25 mg, 0.30 mmol) were added and the solution was allowed to warm to ambient temperature over 18 h. The solvent was removed under reduced pressure to afford a crude oil. The residue was chromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{35}$H$_{40}$N$_4$O$_6$.0.45 H$_2$O, 1.65 HCl) C, 61.73; H, 6.30; N, 8.23 Found C, 61.74; H, 6.30; N, 8.29

TLC: R$_f$=0.55 [10% MeOH(NH$_3$)/90% CH$_2$Cl$_2$]

HPLC (method A): retention time 5.84 min.

FAB MS: m/z 613 (M$^+$+H)

EXAMPLE 42

(±)-1-{1-[4-(1-{2-pyridylamino}-2-propyloxy)-2-methoxybenzoyl]-piperidin-4-yl}-4H-3,1-benzoxazin-2(1H)-one

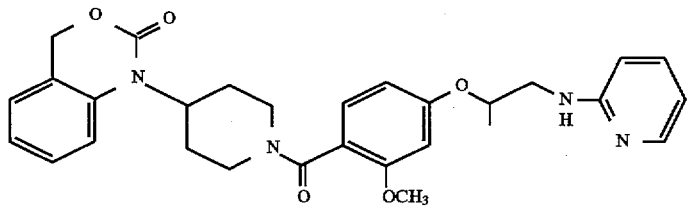

To a stirred solution of (±)-1-{1-[4-(1-carboxaldehyde-2-propyloxy)-2-methoxybenzoyl]-piperidin-4-yl}-4H-3,1-benzoxazin-2(1H)-one (100 mg, 0.23 mmol) from Example 35 in MeOH (500 µL) was added 2-aminopyridine (44 mg, 0.46 mmol) and HOAc (1 drop). The solution was heated to reflux for 2 h and then cooled. NaBH$_3$CN (30 mg, 0.46 mmol) was then added and the solution stirred at ambient temperature for 2.5 h. Additional NaBH$_3$CN (30 mg, 0.46 mmol) and the reaction stirred an additional 16 h. The solvent was then removed under reduced pressure and the crude oil chromatographed on a silica gel column packed in 60:40 CH$_2$Cl$_2$:EtOAc and eluted with same. The appropriate fractions were combined and the solvent was removed under reduced pressure to give an oil which was rechromatographed on a preparative HPLC using a gradient of 95:5 to 5:95 water:acetonitrile (0.1%TFA added). The appropriate fractions were combined and freeze dried giving the title compound as a lyophilized solid.

Analysis calculated for (C$_{29}$H$_{32}$N$_4$O$_5$.1.65 CH$_2$Cl$_2$, 0.10 HCl) C, 55.74; H, 5.40; N, 8.48 Found C, 55.75; H, 5.08; N, 8.26

TLC: R$_f$=0.75 [10% MeOH(NH$_3$)/90% CH$_2$Cl$_2$]

HPLC (method A): retention time 6.39 min.

FAB MS: m/z 517 (M$^+$+H)

EXAMPLE 43

(R)-1-{1-[4-(tetrahydrofuran-3-oxy)-2-methoxybenzoyl]-piperidin-4-yl}-4H-3,1-benzoxazin-2(1H)-one

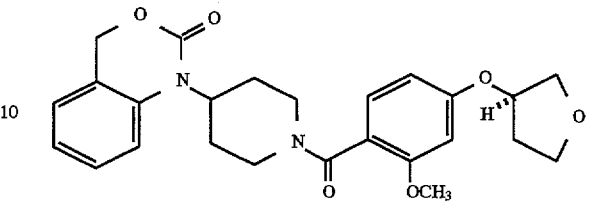

To a stirred solution of Compound A (200 mg, 0.52 mmol) in dry THF (10 mL) was added triphenylphosphine (275 mg, 1.04 mmol) and the solution was cooled to 0° C. A 5 mL volume of S-(+)-3-hydroxytetrahydrofuran (71 µL, 1.04 mmol) and diethyl azodicarboxylate (165 µL, 1.04 mmol) in THF was added dropwise via syringe over 2 hours. The reaction was filtered and the solvent was removed under reduced pressure. The residue was chromatographed on a silica gel column packed in 60:40 CH$_2$Cl$_2$:EtOAc and eluted same. The appropriate fractions were combined and the solvent was removed under reduced pressure to give an oil which was rechromatographed on a silica gel column packed in 98:2 CH$_2$Cl$_2$:MeOH and eluted with same. The appropriate fractions were combined and the solvent was removed under reduced pressure. The residue was chromatographed on a preparative HPLC using a gradient of 95:5 to 5:95 water:acetonitrile (0.1%TFA added). The appropriate fractions were combined and freeze dried giving the title compound as a lyophilized solid.

Analysis calculated for (C$_{25}$H$_{28}$N$_2$O$_6$.0.6 TFA, 0.05 H$_2$O) C, 60.30; H, 5.54; N, 5.37 Found C, 60.33; H, 5.54; N, 5.46

HPLC (method A): retention time 9.32 min.

FAB MS: m/z 467 (M$^+$+H)

EXAMPLE 44

(R)-1-{1-[4-(butyl-2-oxy)-2-methoxybenzoyl]-piperidin-4-yl}-4H-3,1-benzoxazin-2(1H)-one

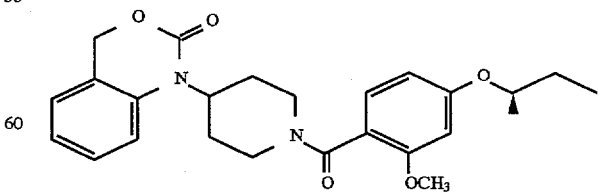

To a stirred solution of Compound A (200 mg, 0.52 mmol) in dry THF (10 mL) was added triphenylphosphine (275 mg, 1.04 mmol) and the solution was cooled to 0° C. A 5 mL volume of the previously prepared (s)-(+)-sec butanol (100 μL, 1.04 mmol) and diethyl azodicarboxylate (165 μL, 1.04 mmol) in THF was added dropwise via syringe over 2 hours. The reaction was filtered and the solvent was removed under reduced pressure and the residue was chromatographed on a silica gel column packed in 60:40 CH$_2$Cl$_2$:EtOAc and eluted with same. The appropriate fractions were combined and the solvent was removed under reduced pressure to give an oil which was rechromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{25}$H$_{30}$N$_2$O$_5$.0.75 H$_2$O) C, 66.42; H, 7.02; N, 6.20 Found C, 66.43; H, 6.63; N, 6.22

HPLC (method A): retention time 11.44 min.

FAB MS: m/z 439 (M$^+$+H)

EXAMPLE 45

(R)-1-{1-[4-(1-{4-pyridyl}ethoxy)-5-fluoro-2-methoxybenzoyl]-piperidin-4-yl}-4H-3,1-benzoxazin-2(1H)-one

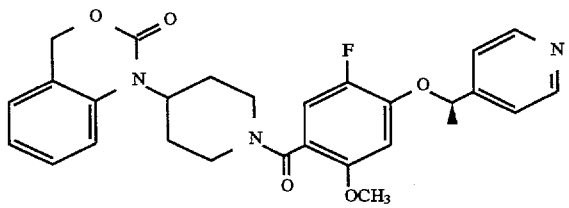

Step 1. A stirred solution of methyl 5-fluoro-2-methoxy-4-hydroxybenzoic acid (250 mg, 1.25 mmol, see Scheme II) in THF (15 mL) was treated with triphenylphosphine (494 mg, 1.88 mmol) and cooled to 0° C. under Argon. To this was added, dropwise over a period of 1 h, a solution of (S)-(–)-1-(4-pyridyl)-ethanol (232 mg, 1.88 mmol) and N,N'-diethylazodicarboxylate (300 μL, 1.88 mmol) in THF (5 mL). The reaction was allowed to warm to ambient temperature overnight with stirring. The reaction was filtered and the solvent was removed under reduced pressure. The residue was chromatographed on a silica gel column packed in 1:1 CH$_2$Cl$_2$:EtOAc and eluted with same. The appropriate fractions were combined and the solvent removed under reduced pressure to afford an impure mixture of 5-fluoro-2-methoxy-4-[1-(S)-(4-pyridyl)ethoxylbenzoate. The residue was rechromatographed on a preparative HPLC using a gradient of 95:5 to 5:95 water:acetonitrile (0.1% TFA added). The appropriate fractions were combined and the solvent removed under reduced pressure to afford the methyl 5-fluoro-2-methoxy-4-[1-(S)-(4-pyridyl)ethoxy]benzoate.

Step 2. To a stirred solution of methyl 5-fluoro-2-methoxy-4-[1-(S)-(4-pyridyl)ethoxy]benzoate (290 mg, 0.95 mmol) in methanol (5 mL) was added aqueous NaOH (396 μL, 3.6M). The reaction was stirred at ambient temperature overnight and then heated to 45° C. in an oil bath for another 24 h. The reaction pH was lowered to pH 3 using 1N HCl and the reaction mixture stripped down under reduced pressure. The white foam was lyophilized from H$_2$O/CH$_3$CN to afford the 5-fluoro-2-methoxy-4-[1-(S)-(4-pyridyl)ethoxy]benzoic acid as a white powder.

Step 3. To a stirred solution of 5-fluoro-2-methoxy-4-[-(S)-(4-pyridyl)ethoxylbenzoic acid (273 mg, 0.95 mmol) and 1-(4-piperidinyl)-1,2-dihydro-4(H)-3,1-benzoxazin-2-one (280 mg, 1.04 mmol, see Scheme III) in DMF (5 mL) was added BOP reagent (461 mg, 1.04 mmol). The reaction was stirred at ambient temperature overnight and the solvent removed under reduced pressure. The residue was dissolved in EtOAc and washed with sat. NaHCO$_3$. The organic phase was dried (MgSO$_4$) and filtered and the solvent removed under reduced pressure. The crude product was chromatographed on a silica gel column packed in 97:3 CH$_2$Cl$_2$:MeOH and eluted with same. The appropriate fractions were combined and the solvent removed under reduced pressure to afford an impure quantity of the desired product. The residue was rechromatographed on a preparative HPLC using a gradient of 95:5 to 5:95 water:acetonitrile (0.1% TFA added). The appropriate fractions were combined and freeze dried giving the title compound as a lyophilized solid.

Analysis calculated for (C$_{28}$H$_{28}$N$_3$O$_6$F.1.65 TFA, 0.20 H$_2$O) C, 53.91; H, 4.34; N, 6.03 Found C, 53.91; H, 4.32; N, 6.21

TLC: R$_f$=0.38 in 97% CH$_2$Cl$_2$:3% MeOH

HPLC (method A): retention time 6.62 min.

FAB MS: m/z 506 (M$^+$+H)

EXAMPLE 46

(R)-1-{1-[4-(1-{N-oxo-4-pyridyl}ethoxy)-5-fluoro-2-methoxybenzoyl]-piperidin-4-yl}-4H-3,1-benzoxazin-2(1H)-one

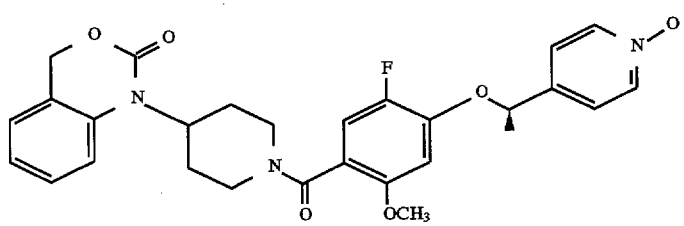

To a stirred solution of the compound of EXAMPLE 45 (90 mg, 0.12 mmol) in CHCl$_3$ (2 mL) was added MCPBA (41 mg, ~55%, 0.13 mmol). The solution was stirred at ambient temperature overnight. The CHCl$_3$ was removed under reduced pressure and the residue redissolved in EtOAc (10 mL). The organic phase was washed with a Na$_2$SO$_3$ solution (2×5 mL), dried (MgSO$_4$) and filtered. The solvent was removed under reduced pressure and the crude residue was chromatographed on a silica gel column packed in 92:8 CH$_2$Cl$_2$:MeOH(NH$_4$OH) and eluted with same. The appropriate fractions were combined and the solvent was removed under reduced pressure to give an oil which was dissolved in acetonitrile:water and freeze dried giving the title compound as a lyophilized solid.

Analysis calculated for $(C_{28}H_{28}N_3O_6F \cdot 1.0\ H_2O)$ C, 62.32; H, 5.60; N, 7.79 Found C, 61.94; H, 5.21; N, 7.60

TLC: $R_f$=0.54 [10% MeOH(NH$_3$)/90% CH$_2$Cl$_2$]

HPLC (method A): retention time 6.74 min.

FAB MS: m/z 522 (M$^+$+H)

EXAMPLE 47

1-{1-[4-(2,2,2-trifluoroethoxy)-2-methoxybenzoyl]-piperidin-4-yl}-4H-3,1-benzoxazin-2(1H)-one

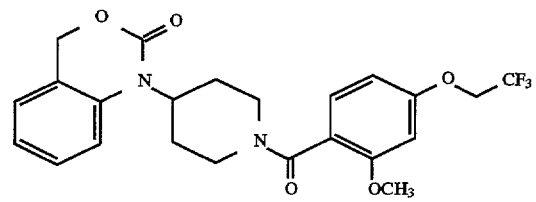

Step 1. A solution of trifluoromethanesulfonyl chloride (640 µL, 6 mmol) in CH$_2$Cl$_2$ (5 mL) was cooled under argon to −78° C. (IPA:dry ice bath). 2,2,2-Trifluoroethanol was added (365 µL, 5 mmol) and triethylamine (834 µL, 6 mmol) was added dropwise. The reaction was stirred for 1.5 hours then warmed to 0° C. for 1 hour. Anhydrous ether (20 mL) was added and the mixture was stirred at 0° C. for 30 minutes. The solids were filtered off and the solvent was removed under reduced pressure with the flask maintained at 0° C. This afforded the 2,2,2-trifluoroethyltriflate as a yellow oil which was used immediately.

Step 2. To a stirred solution of Compound A (400 mg, 1.05 mmol) in dry DMF (10 mL) was added cesium carbonate (2.5 g, 7 eq) followed by the 2,2,2-trifluoroethyltriflate (~6 eq) and the reaction was stirred for 18 hours. The reaction was filtered and the solvent was removed under reduced pressure. The residue was partitioned between EtOAc (100 mL) and 4% aqueous HCl (100 mL). The organic layer was extracted with saturated aqueous sodium bicarbonate (100 mL), water (100 mL), and brine (100 mL) and dried over MgSO$_4$ and filtered. The solvent was removed under reduced pressure to give a foam which was chromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{23}H_{23}N_2F_3O_5 \cdot 0.30\ H_2O)$ C, 58.79; H, 5.06; N, 5.96 Found C, 58.80; H, 5.01; N, 5.98

TLC: $R_f$=0.55 in 5% MeOH/95% CH$_2$Cl$_2$

HPLC (method A): retention time 10.9 min.

FAB MS: m/z 465 (M$^+$+H)

EXAMPLE 48

(±)-1-{1-[4-(carboxyethoxy)-2-methoxybenzoyl]-piperidin-4-yl}-4H-3,1-benzoxazin-2(1H)-one

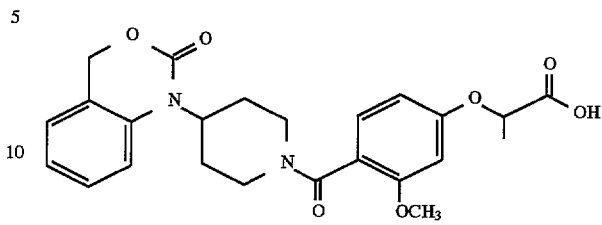

To a stirred solution of LiOH·H$_2$O (17.62 mg, 0.42 mmol) and H$_2$O$_2$ (30%, 52 mL) in THF:H$_2$O (3 mL:1 mL) was added the compound of EXAMPLE 22 (200 mg, 0.42 mmol). The solution was stirred overnight at ambient temperature and then the entire reaction mixture was poured through a column containing prewashed Dowex Ag 8×H+ ion exchange resin (~10 g). The filtrate was collected and the solvent removed under reduced pressure to afford a white foam. The product was dissolved in 9:1 acetonitrile:water and freeze dried giving the title compound as a lyophilized solid.

Analysis calculated for $(C_{24}H_{26}N_2O_7 \cdot 1.70\ CH_2Cl_2,\ 0.55\ MeOH)$ C, 51.14; H, 5.17; N, 4.54 Found C, 51.12; H, 5.14; N, 4.85

TLC: $R_f$=0.10 [20% MeOH(NH$_3$)/80% CH$_2$Cl$_2$]

HPLC (method A): retention time 6.96 min.

FAB MS: m/z 455 (M$^+$+H)

EXAMPLE 49

(±)-1-{1-[4-(1-{aminocarbonyl}ethoxy)-2-methoxybenzoyl]-piperidin-4-yl}-4H-3,1-benzoxazin-2(1H)-one

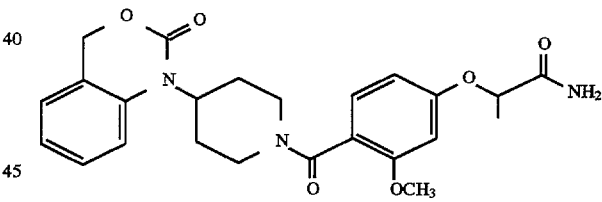

A stirred solution of the compound of EXAMPLE 22 (200 mg, 0.43 mmol) in MeOH (20 mL) was cooled to 0° C. and anhydrous NH$_3$ was bubbled in for 5 minutes. The solution was kept at 0° C. and this procedure was repeated twice, every 30 minutes. The solution was allowed to warm to ambient temperature over 16 h with stirring. The solvent was removed under reduced pressure to give a white solid. The solid was chromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $(C_{24}H_{27}N_3O_6 \cdot 0.4\ H_2O,\ 0.20\ MeOH)$ C, 62.22; H, 6.17; N, 9.00 Found C, 62.21; H, 6.19; N, 9.01

TLC: $R_f$=0.80 [20% MeOH(NH$_3$)/80% CH$_2$Cl$_2$]

HPLC (method A): retention time 6.36 min.

FAB MS: m/z 454 (M$^+$+H)

EXAMPLE 50

(S)-1-{1-[5-fluoro-2-methoxy-4-(tetrahydrofuran-3-oxy)benzoyl]-piperidin-4-yl}-4H-3,1-benzoxazin-2(1H)-one

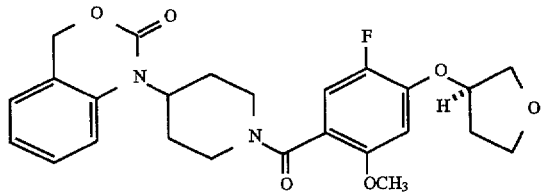

Step 1. To a stirred solution of methyl 2-methoxy-4-hydroxy-5-fluorobenzoate (250 mg, 1.25 mmol) in dry THF (10 mL) was added triphenylphosphine (655 mg, 2.50 mmol) and the solution was cooled to 0° C. A 5 mL volume of S-(+)-3-hydroxytetrahydrofuran (169 mL, 2.25 mmol) and diethyl azodicarboxylate (394 µL, 2.25 mmol) in THF was added dropwise via syringe over 2 hours. The reaction was filtered, the solvent removed under reduced pressure and the residue chromatographed on a silica gel column packed in 60:40 CH$_2$Cl$_2$:EtOAc and eluted with the same. The appropriate fractions were combined and the solvent was removed under reduced pressure to give an oil.

Step 2. To a solution of methyl 2-methoxy-4-R(−)-tetrahydrofuranyloxy-5 fluorobenzoate (320 mg, 1.18 mmol) in THF (10 mL) was added water (5 mL) followed by 2N NaOH (4 mL). The solution was heated at 50° C. under argon for 18 hours. Concentrated HCl was added dropwise to the stirring solution to bring the pH to 4. The solvent was removed under reduced pressure and the residue was partitioned between water and CH$_2$Cl$_2$ and the organic phase was dried with MgSO$_4$, filtered and the solvent removed under reduced pressure to give the acid.

Step 3. To a stirred solution of the 2-methoxy-4-R(−)-tetrahydrofuranyloxy-5 fluorobenzoic acid (250 mg, 0.98 mmol) and 1-(4-piperidinyl)-1,2-dihydro-4(H)-3,1-benzoxazin-2-one (321 mg, 1.2 mmol) in dry, degassed, DMF (20 mL) at room temperature under argon was added HOBT (183 mg, 1.2 mmol) and EDC (229 mg, 1.2 mmol). The pH of the solution was adjusted to 8.5 (wetted E. Merck pH sticks) using diisopropylethylamine. The solution was stirred for 18 hours. The solvent was removed under reduced pressure and the residue was partitioned between CH$_2$Cl$_2$ (100 mL) and 4% aqueous HCl (100 mL). The organic phase was then extracted with water (100 mL), saturated aqueous sodium bicarbonate solution, and brine and dried over MgSO$_4$, filtered and the solvent was removed under reduced pressure. The residue was chromatographed on a silica gel column packed in 98:2 CH$_2$Cl$_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for (C$_{24}$H$_{27}$N$_2$FO$_6$·0.5 H$_2$O, 0.5 CH$_3$CN) C, 62.45; H, 5.95; N, 7.00 Found C, 62.41; H, 6.03; N, 6.96

TLC: R$_f$=0.50 [5% MeOH/95% CH$_2$Cl$_2$]

HPLC (method A): retention time 8.43 min.

FAB MS: m/z 471 (M$^+$+H)

EXAMPLE 51

1-{1-[4-(1,1,2,2-tetrafluoroethoxy)benzoyl]-piperidin-4-yl}-4H-3,1-benzoxazin-2(1H)-one

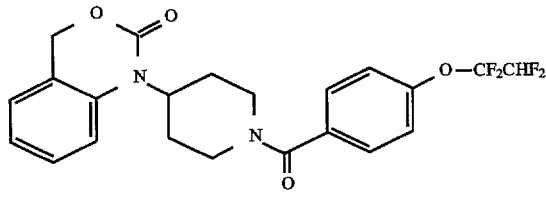

To a stirred solution of 1-(4-piperidinyl)-1,2-dihydro-4(H)-3,1-benzoxazin-2-one hydrochloride (100 mg, 0.37 mmol), 4-(1,1,2,2-tetrafluoroethoxy)benzoic acid (97 mg, 0.41 mmol), HOBT (69 mg, 0.45 mmol), and EDC (132 mg, 0.45 mmol) in DMF (7.5 mL) was added DIEA (0.14 mL, 0.81 mmol). The mixture was stirred at ambient temperature for 18 h and the solvent was removed under reduced pressure. The residue was dissolved in EtOAc (50 mL) and the solution was washed with saturated aqueous NaHCO$_3$ (2×50 mL), dried (Na$_2$SO$_4$), and filtered. The solvent was removed under reduced pressure and the residue was purified by pressurized silica gel column chromatography using 95:5 CH$_2$Cl$_2$:MeOH as eluant. The title compound was obtained as an amorphous solid by lyophilization from CH$_3$CN:H$_2$O.

Analysis calculated for (C$_{22}$H$_{20}$F$_4$N$_2$O$_4$, 0.1 H$_2$O) C, 58.17; H, 4.48; N, 6.17 Found C, 58.22; H, 4.46; N, 6.08

TLC: R$_f$=0.5 in [95:5 CH$_2$Cl$_2$:MeOH]

HPLC (method A): retention time 9.82 min.

FAB MS: m/z 453 (M$^+$+H)

EXAMPLE 52

1-{1-[5-fluoro-2-methoxy-4-(2,2,2-trifluoroethoxy)benzoyl]-piperidin-4-yl}-4(H)-3,1-benzoxazin-2(1H)-one

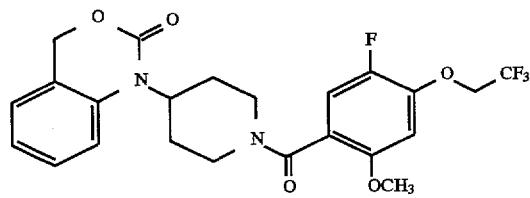

Step 1. A solution of trifluoromethanesulfonyl chloride (800 uL, 7.5 mmole) in CH$_2$Cl$_2$ (6 mL) was cooled under argon to −60° C. (IPA:dry ice bath). 2,2,2-Trifluoroethanol was added (456 uL, 6 mmol) and triethylamine (1.04 uL, 7.5 mmol) was added dropwise. The reaction was stirred for 1.5 hours then warmed to 0° C. for 1 hour. Anhydrous ether (20 mL) was added and the mixture was stirred at 0° C. for 30 minutes. The solids were filtered off and the solvent was removed under reduced pressure with the flask maintained at 0° C. This afforded the 2,2,2-trifluoroethyltriflate as a yellow oil which was used immediately.

Step 2. To a stirred solution of methyl 2-methoxy-4-hydroxy-5-fluorobenzoate (450 mg, 2.25 mmol) in dry, degassed DMF (20 mL) at room temperature under argon was added cesium carbonate (3.3 gm, 10 mmol) followed by the above 2,2,2-trifluoroethyltriflate in 3 mL of dry, degassed DMF and the mixture was stirred for 18 hours. The mixture was filtered through celite and the solvent removed under reduced pressure and the residue was partitioned between EtOAc (100 mL) and 4% aqueous HCL (100 mL). The organic layer was extracted with saturated aqueous sodium bicarbonate (100 mL), water, and brine and dried over $MgSO_4$ and filtered. The solvent was removed under reduced pressure to give a foam which was chromatographed on a silica gel column packed in 98:2 $CH_2Cl_2$:MeOH and eluted with same. The appropriate fractions were combined and the solvent was removed under reduced pressure to give the 2-methoxy-4-trifluoroethoxy-5-fluorobenzoate.

Step 3. The above methoxy-4-trifluoroethoxy-5-fluorobenzoate (420 mg, 1.7 mmol) was dissolved in freshly distilled THF (50 mL) and water was added (20 mL) and 2N NaOH (2 mL) was dropped into the rapidly stirring solution at room temperature. The solution was warmed to 50° C. and stirred rapidly for 18 hours. The biphasic result was reduced to a smaller volume under reduced pressure and water was added to the aqueous residue to a volume of 50 mL and was then acidified with 4 N HCl to a pH of 1–2. The product was extracted with methylene chloride (3×50 mL). The combined organics were extracted with brine (50 mL) and the organic solvent was dried over $MgSO_4$ and filtered and the solvent was removed under reduced pressure to give the desired 4-trifluoroethoxy-5-fluorobenzoic acid.

Step 4. To a stirred solution of 1-(4-piperidinyl)-1,2-dihydro-4(H)-3,1-benzoxazin-2-one hydrochloride (500 mg, 1.8 mmol) in dry, degassed DMF (10 mL) at room temperature, under argon was added HOBT (286 mg, 1.9 mmol) followed by 2-methoxy-4-trifluoroethoxy-5-fluorobenzoic acid (330 mg, 1.9 mmol). To the stirring solution was added EDC (363 mg, 1.9 mmol) and the pH was brought up to pH 8 (tested with wetted E. Merck sticks) via the addition of diisopropylethylamine (1.0 mL). The reaction was allowed to stir for 18 hours. The solvent was removed under reduced pressure and the residue was partitioned between methylene chloride and 4% aqueous HCl and the organic was separated and extracted with water (100 mL), saturated aqueous sodium bicarbonate, and brine and the organic was dried with $MgSO_4$. The slurry was filtered and the solvent removed under reduced pressure. The residue was chromatographed on a silica gel column packed in 98:2 $CH_2Cl_2$:MeOH and eluted with same. The appropriate fractions were combined and the solvent was removed under reduced pressure to give an oil which was dissolved in 9:1 acetonitrile:water and freeze dried giving the title compound as a lyophilized solid.

Analysis calculated for $C_{23}H_{22}N_2F_4O_5$ C 57.26; H 4.60; N 5.81 Found C 57.21; H 4.42; N 5.99

TLC: $R_f$=0.55 (95:5 $CHCl_3$:MeOH)

HPLC (method A): retention time=10.1 min, purity=99%

FAB MS: m/z -483 (M +H$^+$)

EXAMPLE 53

As a specific embodiment of an oral composition, 100 mg of the compound of Example 46 is formulated with sufficient finely divided lactose to provide a total amount of 580 to 590 mg to fill a size O hard gel capsule.

EXAMPLE 54

RAT & HUMAN OT/AVP BINDING ASSAYS

The high affinity binding of [$^3$H]oxytocin (OT) to uterine tissue and [$^3$H]arginine vasopressin (AVP) to liver (AVP-$V_1$ site) and kidney (AVP-$V_2$ site) tissue was determined using crude membrane preparations as described previously [Pettibone, D. J., et al., *J. Pharmacol. and Exper. Ther.*, 256(1): 304–308 (1991)]. Uterine tissue was taken from nonpregnant adult Sprague-Dawley rats (Taconic Farms, Germantown, N.Y.) pretreated (18–24 h) with diethylstilbestrol propionate (DES; 300 µg/kg, i.p.). Uterine tissue (full thickness) was also taken with informed consent from nonlabor pregnant women undergoing cesarean section at 38 to 39 weeks gestation (Oregon Health Sciences Center, Portland, Oreg.). Liver and kidney medulla samples were taken from male rats and from human surgical and early postmortem donors (National Disease Research Interchange, Philadelphia Pa.; Analytical Biological Services, Wilmington, Del.).

Competition studies were conducted at equilibrium using 1 nM [$^3$H]OT or 0.5 nM [$^3$H]AVP in the following buffer: 50 mM Tris, 5 mM $MgCl_2$, 0.1% bovine serum albumin. Nonspecific binding was determined using 1 µM unlabeled OT or AVP in their respective assays. The binding reactions were initiated by the addition of tissue preparation and terminated by filtration using a Skatron cell harvester (model 7019, Skatron, Inc., Sterling, Va.). Ki values were calculated for each compound using three to six separate $IC_{50}$ determinations ($K_i=IC_{50}/[1-c/K_d]$); [Cheng, Y.-C.; Prusoff, W. H.; *Biochem. Pharmacol.* 22:3099 (1973)] with mean $K_d$ values obtained from replicate (n=3) equilibrium saturation binding assays (10 point, 100 fold concentration range): $^3$H]OT rat uterus, 0.69 nM; human myometrium, 1.1 nM; [$^3$H]AVP: rat liver, 0.21 nM; rat kidney, 0.27 nM; human liver, 0.27 nM; human kidney, 1.4 nM. Computer analysis of the saturation assays by EBDA/LIGAND [McPherson, G. A.: Kinetic, Ebda, Ligand, Lowry: A Collection of Radioligand Binding Analysis Programs, Elsevier Science Publishers, Amsterdam (1985)] indicated that both radioligands apparently bound to single sites in all tissues examined. The final protein concentration for the various tissues in each assay ranged from 150 to 300 µg/ml [Lowry, P. H.; Rosebrough, N. J.; Farr, A. L.; Randall, R. J.; *J. Biol. Chem.*, 193:265–275 (1951)].

$IC_{50}$ values were determined for the [$^3$H]OT and [$^3$H]AVP binding assays by linear regression of the relation log concentration of compound vs. percent inhibition of specific binding. Data is either reported as a given percentage of inhibition at a specified concentration, or if an $IC_{50}$ was calculated, as a nanomolar concentration. Representative compounds of the present invention were found to have $IC_{50}$ values in the range of 5–500 nM.

The oxytocin antagonistic effect of the compounds of the present invention can be further evaluated according to the in vitro and/or in vivo functional assays described in detail in D. J. Petribone et al., *Drug Devel. Res.* 1993, 30, 129–142.

While the foregoing specification teaches the principles of the present invention, with examples for the purpose of illustration, it will be understood that the practice of the invention encompasses all of the usual variations, adaptions and/or modifications as come within the scope of the following claims and their equivalents.

What is claimed is:
1. A compound of the formula (I)

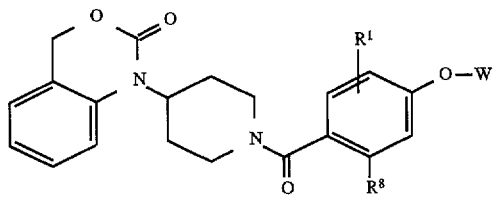

wherein
R¹ is selected from hydrogen or halogen;
W is selected from

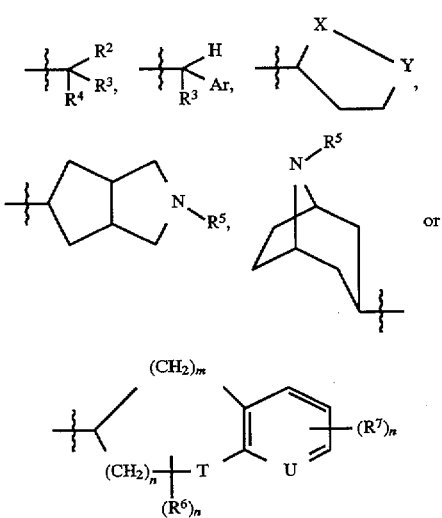

$R^2$ is selected from hydrogen, halogen or $C_{1-5}$ alkyl;
$R^3$ is selected from hydrogen, halogen, $C_{1-5}$ alkyl or Ar;
$R^4$ is selected from $CONH_2$, $CO_2R^7$, CN, $CH_2OR^7$, $CH(CH_3)OH$, $CH_2N(R^7)_2$,

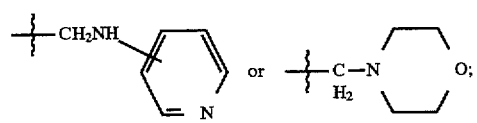

$R^5$ is selected from hydrogen, $COCH_3$, $CO_2C(CH_3)_3$ or

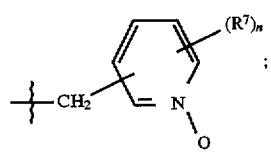

$R^6$ and $R^7$ are each independently selected from hydrogen or $C_{1-5}$ alkyl;
$R^8$ is selected from hydrogen or $C_{1-5}$ alkoxy;
T is selected from O, $CH_2$ or $SO_2$;
U is selected from CH or N;
X is selected from $(CH_2)_n$ or $CH(Ph)CH_2$;
Y is selected from O, $CH_2$, $CHNH_2$, $SO_2$, $CHNHCOCH_3$, or CO;
Ar is selected from naphthyl, tetrazolyl, thiazolyl, imidazolyl, pyrazinyl, or pyrimidinyl;

m is an integer of from zero to one;
n is an integer of from zero to three;
and the pharmaceutically acceptable salts thereof.
2. The compound of claim 1, wherein
R¹ is selected from hydrogen or fluorine;
R² is selected from hydrogen or fluorine;
R³ is selected from hydrogen, fluorine, methyl or phenyl;
$R^4$ is selected from $CONH_2$, $CO_2H$, $CO_2CH_3$, CN, $CH_2OH$, $CH_2OCH_3$, $CH(CH_3)OH$, $CH_2N(Et)_2$,

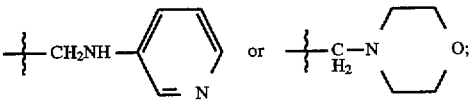

$R^6$ is selected from hydrogen or methyl;
$R^7$ is selected from hydrogen, methyl, ethyl or isopropyl;
$R^8$ is methoxy;
and the pharmaceutically acceptable salts thereof.
3. The compound of claim 2 of the formula

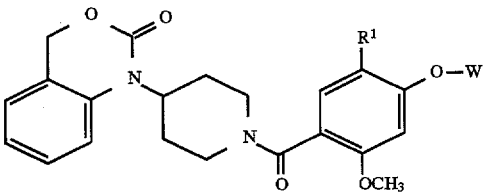

and the pharmaceutically acceptable salts thereof.
4. The compound of claim 3 wherein W is selected from

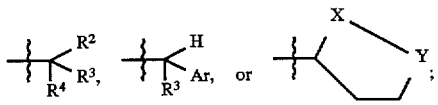

and the pharmaceutically acceptable salts thereof.
5. The compound of claim 4, selected from

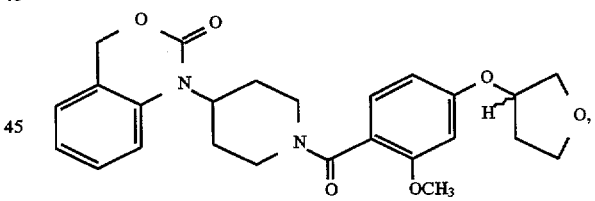

or

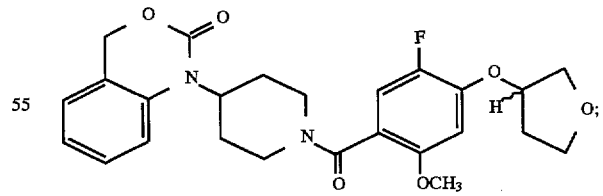

and the pharmaceutically acceptable salts thereof.
6. A pharmaceutical composition comprising a pharmaceutically acceptable carrier and a therapeutically effective amount of the compound of claim 1.
7. A method of eliciting an oxytocin antagonizing effect in a mammal in need thereof, comprising administering to the mammal a therapeutically effective amount of the compound of claim 1.

8. A method of treating preterm labor in a mammal in need thereof, comprising administering to the mammal a therapeutically effective amount of the compound of claim 1.

9. A method of stopping labor preparatory to cesarean delivery in a mammal in need thereof, comprising administering to the mammal a therapeutically effective amount of the compound of claim 1.

10. A method of treating dysmenorrhea in a mammal in need thereof, comprising administering to the mammal a therapeutically effective amount of a compound of claim 1.

11. A method of increasing fertility and embryonic survival in a farm animal, comprising administering to the farm animal a therapeutically effective amount of the compound of claim 1.

12. A method for improving survival of a farm animal neonate comprising controlling timing of parturition to effect delivery of the neonate during daylight hours by administering to a farm animal which is expected to deliver the neonate within 24 hours a therapeutically effective amount of the compound of claim 1.

13. A method of controlling the timing of estrus in a farm animal, comprising administering to the farm animal a therapeutically effective amount of the compound of claim 1.

* * * * *